(12) United States Patent
Wu et al.

(10) Patent No.: US 8,309,324 B2
(45) Date of Patent: Nov. 13, 2012

(54) **PROMOTERS AND PROTEINS FROM *CLOSTRIDIUM THERMOCELLUM* AND USES THEREOF**

(75) Inventors: J. H. David Wu, Pittsford, NY (US); Michael Newcomb, Rochester, NY (US)

(73) Assignee: University of Rochester, Rochester, NY (US)

( * ) Notice: Subject to any disclaimer, the term of this patent is extended or adjusted under 35 U.S.C. 154(b) by 1384 days.

(21) Appl. No.: 11/271,287

(22) Filed: Nov. 10, 2005

(65) Prior Publication Data
US 2006/0105442 A1 May 18, 2006

Related U.S. Application Data

(60) Provisional application No. 60/626,686, filed on Nov. 10, 2004, provisional application No. 60/626,661, filed on Nov. 10, 2004.

(51) Int. Cl.
*C12P 21/02* (2006.01)

(52) U.S. Cl. ............... 435/69.1; 435/320.1; 435/252.33; 435/254.21; 435/325; 435/235.1; 435/161; 536/24.1

(58) Field of Classification Search ..................... None
See application file for complete search history.

(56) References Cited

U.S. PATENT DOCUMENTS

| | | | | |
|---|---|---|---|---|
| 4,863,855 | A | * | 9/1989 | Inouye et al. ............... 435/69.1 |
| 5,514,584 | A | * | 5/1996 | Lastick et al. ............. 435/252.3 |
| 5,807,717 | A | * | 9/1998 | Joyce ........................... 435/91.1 |

OTHER PUBLICATIONS

Mishra et al., J. Bacteriol., vol. 173, 1991, pp. 80-85.*
Sakka et al., Agric. Biol. Chem., vol. 55 (1991) pp. 347-350.*
Genbank Accession No. ZP_00313231 (Jun. 17, 2004).
Newcomb et al., "Transcription Regulation of the *Clostridium thermocellum* Cellulases," (Abstract), MIE Bioforum (Nov. 12, 2003).
Fuchs et al., "Lic16A of *Clostridium thermocellum*, a Non-Cellulosomal, Highly Complex Endo-Beta-1, 3-Glucanase Bound to the Outer Cell Surface," Microbiology 149:1021-1031 (2003).
Demain et al., "Cellulase, Clostridia, and Ethanol," Microbiol. Mol. Biol. Rev. 69(1):124-154 (2005).
Michael Newcomb et al., University of Rochester, "Transcription Regulation of the Clostridium thermocellum Cellulases," Oral Presentation at the MIE Bioforum 2003: Biotechnology of Lignocellulose Degradation and Biomass Utilization (Nov. 12, 2003).

* cited by examiner

*Primary Examiner* — James S Ketter
(74) *Attorney, Agent, or Firm* — LeClairRyan, a Professional Corporation

(57) ABSTRACT

The present invention relates to an inducible and a high expression nucleic acid promoter isolated from *Clostridium thermocellum*. These promoters are useful for directing expression of a protein or polypeptide encoded by a nucleic acid molecule operably associated with the nucleic acid promoters. The present invention also relates to nucleic acid constructs including the *C. thermocellum* promoters, and expression vectors and hosts containing such nucleic acid constructs. The present invention also relates to protein isolated from *Clostridium thermocellum*, including a repressor protein. The present invention also provides methods of using the isolated promoters and proteins from *Clostridium thermocellum*, including methods for directing inducible in vitro and in vivo expression of a protein or polypeptide in a host, and methods of producing ethanol from a cellulosic biomass.

51 Claims, 17 Drawing Sheets

Cellobiose grown     Cotton grown
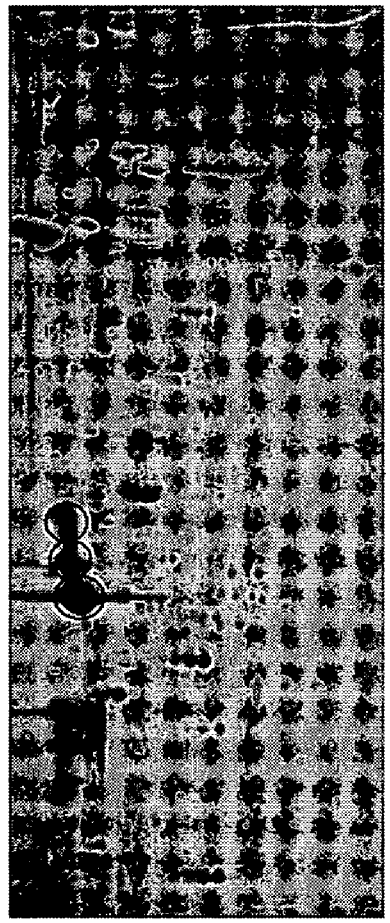
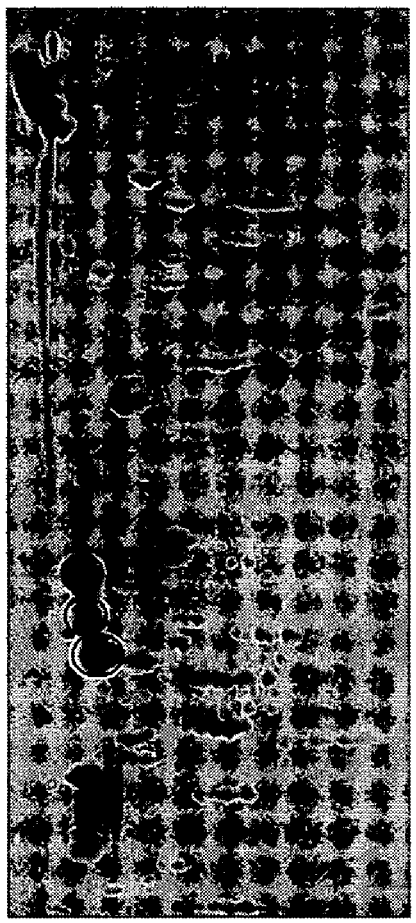
59
Figure 4

```
CelR1           --MAKKVTMEFIANQLGITKNTVSLALRNMPGVSEKTRKEILRTAEKYGYIYKKSNSKNS
CelR2           ------MNSKDIAKIVGVSRSTVSRVINNYPDIPQATREKVLKAIKEYNYYPNASARRLA
CelR3           ------MTSEEIAKLCGVSRATVSRVINNSPNVKEETRQKILAVIKEKNYVPIAPARRLA
CelR (T. fusca) MERRRRPTLEMVAALAGVGRGTVSRVINGSDQVSPATREAVKRAIKELGYVPNRAARTLV
LacI (E. coli)  ---MKPVTLYDVAEYAGVSYQTVSRVVNQASHVSAKTREKVEAAMAELNYIPNRVAQQLA CelR1           KSNSRTGSICLMLSNDTKNSVGFFS-----------FIQYGVESEGKRN--GLNTILYCF
CelR2           GMKSSTLGIFIIDIKDNEKPHHVIENNEDLLYGNSYFSPFINAFIDQSNKAQYHVLVSTI
CelR3           GIDSNIIGLFVLDIDISESKSRVSES---------TYFSRLINLIIDQANNFGFQVLVSII
CelR            TRRTDTVALVVSENNQKLFAEPFYAG---------IVLGVGVALSER---GFQFVLATG
LacI            GKQSLLIGVATSSLALHAPSQIVAA---------------IKSRADQLG--ASVVVSMVE CelR1           DDNKEFQPPVCIRDG-IVSGIITLG--RISRKTVSSIISLNLPLVIVDDFFDDIKAS---
CelR2           YSSDELWKIQSAFYEKRIDGAVIIGSSSIDYSKIFEIMDKDSITVAVDLDMEKENTG-TV
CelR3           TSQKQLSEIRNLFMSRTIFSGIFIG-AFNDEIQLDDDIIMQHPTIIIDRQSERMVKKPNR
CelR            RSGIEHERLGGYLAGQHVDGVLLLS--LHRDCPLPQMLDEAGVPYVYGGRPLGVPEE-QV
LacI            RSGVEACKAAVHNLLAQRVSGLIINYPLDDQDAIAVEAACTNVPALFLDVSDQTPIN---

CelR1           -YVLTDNLSGGYTATEYLIKSGHRSIGFFGDIFASPSFFDRYMGYLKAHVQYNLPVNSSF
CelR2           MSVNINNYGGVSDAIDYLVELGHKDIAVITGDLNKLSGKIRFESFKDALLRHGLPLNNDF
CelR3           LVVNLDNFEGAYNATQFLIKLGHTRIGHISGDLRKLSGIERYEGYKKALEDAGLGFDKNL
CelR            SYVDIDNIGGGRQATQRLIETGHRRIATIAGFQDMVAGVERLQGYREALLAAGMEYDETL
LacI            -SIIFSHEDGTRLGVEHLVALGHQQIALLAGFLSSVSARLRLAGWHKYLTRN--QIQPIA

CelR1           SIIDKNMAVLLHEGVDKVVDELKKIPQLPTAMFCCNDVEAIALYKAFSVMGISVPDDISI
CelR2           IAYGDFTENSGYEGMKKILASGKKP----TAVFTSNDTMAIGAYRAIKEYGLKIPEDISV
CelR3           VREGNFLDDSGYRLAREILKEN--V----TAIFCANDVMAISAIKAIKETGLSVPDDISV
CelR            VSYGDFTYDSGVAAMRELLDRAPDV----DAVFAASDLMGLAALRVLRASGRRVPEDVAV
LacI            EREGDWSAMSGFQQTMQMLNEGIVP----TAMLVANDQMALGAMRAITESGLRVGADISV

CelR1           IGFDDIESSTSVSPELTTMHINKEAMGERAVKKLIEKMNGQESMDEKIVLPVTLIERQSV
CelR2           MGFDNSYISQYMSPPLTTVNVSLPEIAKCSIELLLDSINNKEIKNRQKTVNVQIVKRNSC
CelR3           IGFDNTAIGNYIMPALTTVNAPLEHIAEACIESLKYFCEHKHFKQKEIRVKTDLIIRDST
CelR            VGYDDSTVAEHAEPPMTSVNQPTELMGREMARLLVDRITGETTEPVRLVLETHLMVRESG
LacI            VGYDDTEDSSCYIPPSTTIKQDFRLLGQTSVDRLLQLSQGQAVKGNQ-LLPVSLVKRKTT

CelR1           KRIG--------------------------------
CelR2           KKIV--------------------------------
CelR3           KRALEF------------------------------
CelR            ------------------------------------
LacI            LAPNTQTASPRALADSLMQLARQVSRLESGQ
```

Figure 5

SEQUENCE LISTING

<160> NUMBER OF SEQ ID NOS: 42

<210> SEQ ID NO 1
<211> LENGTH: 300
<212> TYPE: DNA
<213> ORGANISM: C. thermocellum

<400> SEQUENCE: 1

```
aatcaataaa attataacat attacttcaa aagtggggac aaaaaagaac aaaaaaattg      60
aaattttgat gaaaaataca agatatgaat taagtgggcc gaataaaaac tggacagaga     120
agaagaaaac gtgatataat taaattagaa tgaacgcgcg tacattattg aataatccag     180
tgttaaatgg tttcagttta cgatttcaaa tgtttatatc caatttacat ttaaaaacat     240
acaaaacatc aaaagtattt ataccaata tttaaaacac aatatttcag gaggaaaaaa      300
```

<210> SEQ ID NO 2
<211> LENGTH: 1038
<212> TYPE: DNA
<213> ORGANISM: C. thermocellum

<400> SEQUENCE: 2

```
atgaccagtg aagaaatagc aaaattatgt ggtgtttcca gagccacggt atccagggtt      60
attaacaaca gtcccaacgt aaaagaggaa acgcggcaaa agattctggc agtgataaaa     120
gaaaaaatt atgttccgat agcgccggca cggcgtttgg ccgggataga cagcaatata     180
attggcctgt ttgttttgga tattgacata tctgagtcaa agtcaagggt ctcggaaagt     240
acatactttt cacggctgat aaatctgata atagaccagg caaacaattt tggcttttcaa    300
gtattggtgt caattataac ttcacagaaa cagctgagtg aaattagaaa tctcttcatg     360
agcagaacca ttttcagcgg catttttatc ggtgcgttca atgatgaaat ccaacttgat     420
gatgatatta aatgcaaca tcccacaatt attattgacc gccaatcaga aaggatggtg     480
aaaaagccaa acagattggt tgtaaacctg gacaactttg agggtgctta taatgcgaca     540
cagttttttga ttaaattggg gcataccaga attgggcaca tatccgggga ccttagaaaa     600
ctttcgggca tagaacgcta tgaaggatac aaaaaagcat tggaagatgc aggattaggt     660
tttgacaaaa atttggttcg tgaagggaac ttccttgatg acagcggcta taggcttgca     720
cgtgagatat aaaagagaa cgtgacggct atttttctgt gccaatgatgt aatggcaatt     780
agtgcaatta aagccataaa agaaacgggt ttgagtgtac cggatgatat atctgtaata     840
gggtttgata atacagcaat cggaaattat atcatgcctg cattgacaac tgtgaacgcg     900
ccgttggagc atattgcaga agcatgtatt gagtcattga aatacttttg cgagcacaaa     960
cattttaaac aaaaggaaat cagggttaaa accgatttga taatccggga ttcaaccaag    1020
agggctttgg aattctga                                                  1038
```

<210> SEQ ID NO 3
<211> LENGTH: 345
<212> TYPE: PRT
<213> ORGANISM: C. thermocellum

<400> SEQUENCE: 3

```
Met Thr Ser Glu Glu Ile Ala Lys Leu Cys Gly Val Ser Arg Ala Thr
 1               5                  10                  15
Val Ser Arg Val Ile Asn Asn Ser Pro Asn Val Lys Glu Glu Thr Arg
            20                  25                  30
```

-continued

```
Gln Lys Ile Leu Ala Val Ile Lys Glu Lys Asn Tyr Val Pro Ile Ala
             35                  40                  45
Pro Ala Arg Arg Leu Ala Gly Ile Asp Ser Asn Ile Ile Gly Leu Phe
 50                  55                  60
Val Leu Asp Ile Asp Ile Ser Glu Ser Lys Ser Arg Val Ser Glu Ser
 65                  70                  75                  80
Thr Tyr Phe Ser Arg Leu Ile Asn Leu Ile Ile Asp Gln Ala Asn Asn
             85                  90                  95
Phe Gly Phe Gln Val Leu Val Ser Ile Ile Thr Ser Gln Lys Gln Leu
            100                 105                 110
Ser Glu Ile Arg Asn Leu Phe Met Ser Arg Thr Ile Phe Ser Gly Ile
            115                 120                 125
Phe Ile Gly Ala Phe Asn Asp Glu Ile Gln Leu Asp Asp Asp Ile Ile
130                 135                 140
Met Gln His Pro Thr Ile Ile Asp Arg Gln Ser Glu Arg Met Val
145                 150                 155                 160
Lys Lys Pro Asn Arg Leu Val Val Asn Leu Asp Asn Phe Glu Gly Ala
                165                 170                 175
Tyr Asn Ala Thr Gln Phe Leu Ile Lys Leu Gly His Thr Arg Ile Gly
            180                 185                 190
His Ile Ser Gly Asp Leu Arg Lys Leu Ser Gly Ile Glu Arg Tyr Glu
            195                 200                 205
Gly Tyr Lys Lys Ala Leu Glu Asp Ala Gly Leu Gly Phe Asp Lys Asn
210                 215                 220
Leu Val Arg Glu Gly Asn Phe Leu Asp Asp Ser Gly Tyr Arg Leu Ala
225                 230                 235                 240
Arg Glu Ile Leu Lys Glu Asn Val Thr Ala Ile Phe Cys Ala Asn Asp
                245                 250                 255
Val Met Ala Ile Ser Ala Ile Lys Ala Ile Lys Glu Thr Gly Leu Ser
                260                 265                 270
Val Pro Asp Asp Ile Ser Val Ile Gly Phe Asp Asn Thr Ala Ile Gly
            275                 280                 285
Asn Tyr Ile Met Pro Ala Leu Thr Thr Val Asn Ala Pro Leu Glu His
            290                 295                 300
Ile Ala Glu Ala Cys Ile Glu Ser Leu Lys Tyr Phe Cys Glu His Lys
305                 310                 315                 320
His Phe Lys Gln Lys Glu Ile Arg Val Lys Thr Asp Leu Ile Ile Arg
                325                 330                 335
Asp Ser Thr Lys Arg Ala Leu Glu Phe
                340                 345

<210> SEQ ID NO 4
<211> LENGTH: 300
<212> TYPE: DNA
<213> ORGANISM: C. thermocellum

<400> SEQUENCE: 4
ttaatatgcc gaccacgttg caattcccgt caaataatgc attttgcagc cgacgaaaca    60
ggcaagataa ctgtattggc tataaatgtt tcaagcagcg gtatattttg cctcccggta   120
aaattaatac aataagctaa aaaactgacg taggataagc aaaacggcgc aatttgagtt   180
gtaacgtaat attttcacta aaaatagtaa ttatttcatg ttgtttttttt ttagattaat   240 ttataatata atttattgta taagcaatat cttaattatc attaaggggg gaaaaaaact   300

<210> SEQ ID NO 5
```

```
<211> LENGTH: 1380
<212> TYPE: DNA
<213> ORGANISM: C. thermocellum

<400> SEQUENCE: 5
atgctcaaga aggtaatcgc attaatgttg gttgctgtta tggctttaag tctggcagca      60
tgtggtggtg gaggaggaaa tactacgact tcaccgcaac caaacgattc ccaaaattcg     120
cctgattcag gaacaaagaa ggacccagta aaattgacca tgtggatcat gcctaacagt     180
gacacaccgg accaggatct tttgaaagtt gttaagccat tcacagatgc taatcctcat     240
atcacagttg aacctacagt tgttgactgg agtgcagctt tgacaaagat cacagctgct     300
gctacaagtg gtgaagctcc tgacattaca caggttggtt ccacttggac agctgctatc     360
ggtgcaatgg aaggtgcatt ggttgagctt accggaaaaa tcgatacaag tgctttcgtt     420
gaatcaactc tgcagtcagc ttatatcaaa ggcacagaca agatgttcgg tatgccttgg     480
tttactgaaa caagagctct cttctacaga aaagacgctt gcgaaaaagc aggtgtaaat     540
cctgaaacag atttcgcaac ttgggacaaa ttcaaagatg ctctcaagaa actcaacggt     600
attgaagttg acggcaagaa actggttgca ctgggtatgc cgggtaagaa cgactggaac     660
gttgttcata acttctcatg gtggatttac ggtgccggcg gagactttgt aaacgaagaa     720
ggtacacaag ctactttctc aagcgaaaat gctcttaaag gtatcaaatt ctattcagaa     780
cttgctgttg aaggtttgat ggatgagcct tcacttgaaa agaatacaag tgacattgag     840
tccgcatttg gtgacggtgc atacgctact gcattcatgg gtccttgggt tatttcatct     900
tacacaaaga ataaagaaga aaacggtaac gaccttatcg acaaaattgg tgttactatg     960
gttcctgaag gacctgcagg aagatatgca ttcatgggtg aagtaaccct tgtaatattc    1020
aactcatcaa gaacaaggga tgaagccgtt gaacttctca gttctttgc tagcaaagaa    1080
gctcaggttg aatactcaaa ggttagcaag atgcttccgg ttgttaaagc ggcttacgaa    1140
gatccatact ttgaagattc attgatgaaa gtattcaaag aacaggtaga caaatatggt    1200
aaacactatg catcagttcc tggttgggct tctgcagaag ttatcttctc agaaggtctc    1260
agcaagatct gggataacgt tatggaagtt gatggtgcat acagctacga caagactgta    1320
caaatcgtaa aagatgttga agtcaaatc aaccaaatat tgcaagaaac aagcaaataa    1380

<210> SEQ ID NO 6
<211> LENGTH: 459
<212> TYPE: PRT
<213> ORGANISM: C. thermocellum

<400> SEQUENCE: 6

Met Leu Lys Lys Val Ile Ala Leu Met Leu Val Ala Val Met Ala Leu
 1               5                  10                  15

Ser Leu Ala Ala Cys Gly Gly Gly Gly Asn Thr Thr Thr Ser Pro
                 20                  25                  30

Gln Pro Asn Asp Ser Gln Asn Ser Pro Asp Ser Gly Thr Lys Lys Asp
             35                  40                  45

Pro Val Lys Leu Thr Met Trp Ile Met Pro Asn Ser Asp Thr Pro Asp
         50                  55                  60

Gln Asp Leu Leu Lys Val Val Lys Pro Phe Thr Asp Ala Asn Pro His
 65                  70                  75                  80

Ile Thr Val Glu Pro Thr Val Val Asp Trp Ser Ala Ala Leu Thr Lys
                 85                  90                  95

Ile Thr Ala Ala Ala Thr Ser Gly Glu Ala Pro Asp Ile Thr Gln Val
            100                 105                 110
```

Gly Ser Thr Trp Thr Ala Ala Ile Gly Ala Met Glu Gly Ala Leu Val
            115                 120                 125

Glu Leu Thr Gly Lys Ile Asp Thr Ser Ala Phe Val Glu Ser Thr Leu
    130                 135                 140

Gln Ser Ala Tyr Ile Lys Gly Thr Asp Lys Met Phe Gly Met Pro Trp
145                 150                 155                 160

Phe Thr Glu Thr Arg Ala Leu Phe Tyr Arg Lys Asp Ala Cys Glu Lys
                165                 170                 175

Ala Gly Val Asn Pro Glu Thr Asp Phe Ala Thr Trp Asp Lys Phe Lys
            180                 185                 190

Asp Ala Leu Lys Lys Leu Asn Gly Ile Glu Val Asp Gly Lys Lys Leu
        195                 200                 205

Val Ala Leu Gly Met Pro Gly Lys Asn Asp Trp Asn Val Val His Asn
    210                 215                 220

Phe Ser Trp Trp Ile Tyr Gly Ala Gly Gly Asp Phe Val Asn Glu Glu
225                 230                 235                 240

Gly Thr Gln Ala Thr Phe Ser Ser Glu Asn Ala Leu Lys Gly Ile Lys
                245                 250                 255

Phe Tyr Ser Glu Leu Ala Val Glu Gly Leu Met Asp Glu Pro Ser Leu
            260                 265                 270

Glu Lys Asn Thr Ser Asp Ile Glu Ser Ala Phe Gly Asp Gly Ala Tyr
        275                 280                 285

Ala Thr Ala Phe Met Gly Pro Trp Val Ile Ser Ser Tyr Thr Lys Asn
    290                 295                 300

Lys Glu Glu Asn Gly Asn Asp Leu Ile Asp Lys Ile Gly Val Thr Met
305                 310                 315                 320

Val Pro Glu Gly Pro Ala Gly Arg Tyr Ala Phe Met Gly Gly Ser Asn
                325                 330                 335

Leu Val Ile Phe Asn Ser Ser Lys Asn Lys Asp Glu Ala Val Glu Leu
            340                 345                 350

Leu Lys Phe Phe Ala Ser Lys Glu Ala Gln Val Glu Tyr Ser Lys Val
        355                 360                 365

Ser Lys Met Leu Pro Val Val Lys Ala Ala Tyr Glu Asp Pro Tyr Phe
    370                 375                 380

Glu Asp Ser Leu Met Lys Val Phe Lys Glu Gln Val Asp Lys Tyr Gly
385                 390                 395                 400

Lys His Tyr Ala Ser Val Pro Gly Trp Ala Ser Ala Glu Val Ile Phe
                405                 410                 415

Ser Glu Gly Leu Ser Lys Ile Trp Asp Asn Val Met Glu Val Asp Gly
            420                 425                 430

Ala Tyr Ser Tyr Asp Lys Thr Val Gln Ile Val Lys Asp Val Glu Ser
        435                 440                 445

Gln Ile Asn Gln Ile Leu Gln Glu Thr Ser Lys
    450                 455

<210> SEQ ID NO 7
<211> LENGTH: 40
<212> TYPE: PRT
<213> ORGANISM: C. thermocellum

<400> SEQUENCE: 7

Met Leu Lys Lys Val Ile Ala Leu Met Leu Val Ala Val Met Ala Leu
  1               5                  10                  15

Ser Leu Ala Ala Cys Gly Gly Gly Gly Asn Thr Thr Thr Ser Pro
            20                  25                  30

Gln Pro Asn Asp Ser Gln Asn Ser
        35                  40

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 8
gcgcgatatc accagtgaag aaatagcaaa atta                            34

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 9
gcgcctcgag gaattccaaa gccctcttgg tt                              32

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 10
ccgaataaaa actggacaga g                                          21

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 11
tcctcctgaa atattgtgtt tta                                        23

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 12
tgaaaccatt taacactgga ttat                                       24

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 13

```
gtttacgatt tcaaatgttt atatc                                          25
```

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 14

```
aatgaacgcg cgtacatt                                                  18
```

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 15

```
aatgtacgcg cgttcatt                                                  18
```

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 16

```
aattcgaagc aacgcgaaga ac                                             22
```

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 17

```
gcgggactta acccaacatc tc                                             22
```

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 18

```
cgggaacata ttgcctttga ac                                             22
```

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 19

```
ggtggaatca atttccctga ttg                                            23
```

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 20
gggcatagaa cgctatgaag ga                                              22

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 21
tatagccgct gtcatcaagg aa                                              22

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 22
ttgaccaagg tccgaacaga a                                               21

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 23
ttcaaacctg cgctcattaa ca                                              22

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 24
tcactgcttg atcctcgttt gt                                              22

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 25
acgccatttc tcttgcaatc tc                                              22

<210> SEQ ID NO 26

```
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 26
ggtatccata aaggtgccca ga                                                  22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 27
attcaccgaa gtgcttgtac cc                                                  22

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 28
tctggattcc cagaacacca ac                                                  22

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 29
cctcaggcaa accaaacttc ac                                                  22

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 30
ccgaataaaa actggacaga ag                                                  22

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 31
ccagtgggct ttctgatgc                                                      19

<210> SEQ ID NO 32
<211> LENGTH: 342
<212> TYPE: PRT
```

<213> ORGANISM: C. thermocellum

<400> SEQUENCE: 32

```
Met Ala Lys Lys Val Thr Met Glu Phe Ile Ala Asn Gln Leu Gly Ile
  1               5                  10                  15

Thr Lys Asn Thr Val Ser Leu Ala Leu Arg Asn Met Pro Gly Val Ser
             20                  25                  30

Glu Lys Thr Arg Lys Glu Ile Leu Arg Thr Ala Glu Lys Tyr Gly Tyr
         35                  40                  45

Ile Tyr Lys Lys Ser Asn Ser Lys Asn Ser Lys Ser Asn Ser Arg Thr
 50                  55                  60

Gly Ser Ile Cys Leu Met Leu Ser Asn Asp Thr Lys Asn Ser Val Gly
 65                  70                  75                  80

Phe Phe Ser Phe Ile Gln Tyr Gly Val Glu Ser Glu Gly Lys Arg Asn
                 85                  90                  95

Gly Leu Asn Thr Ile Leu Tyr Cys Phe Asp Asp Asn Lys Glu Phe Gln
            100                 105                 110

Pro Pro Val Cys Ile Arg Asp Gly Ile Val Ser Gly Ile Ile Thr Leu
            115                 120                 125

Gly Arg Ile Ser Arg Lys Thr Val Ser Ser Ile Ile Ser Leu Asn Leu
130                 135                 140

Pro Leu Val Ile Val Asp Asp Phe Phe Asp Ile Lys Ala Ser Tyr
145                 150                 155                 160

Val Leu Thr Asp Asn Leu Ser Gly Gly Tyr Thr Ala Thr Glu Tyr Leu
                165                 170                 175

Ile Lys Ser Gly His Arg Ser Ile Gly Phe Phe Gly Asp Ile Phe Ala
            180                 185                 190

Ser Pro Ser Phe Phe Asp Arg Tyr Met Gly Tyr Leu Lys Ala His Val
            195                 200                 205

Gln Tyr Asn Leu Pro Val Asn Ser Ser Phe Ser Ile Ile Asp Lys Asn
210                 215                 220

Met Ala Val Leu Leu His Glu Gly Val Asp Lys Val Val Asp Glu Leu
225                 230                 235                 240

Lys Lys Ile Pro Gln Leu Pro Thr Ala Met Phe Cys Cys Asn Asp Val
                245                 250                 255

Glu Ala Ile Ala Leu Tyr Lys Ala Phe Ser Val Met Gly Ile Ser Val
            260                 265                 270

Pro Asp Asp Ile Ser Ile Ile Gly Phe Asp Asp Ile Glu Ser Ser Thr
            275                 280                 285

Ser Val Ser Pro Glu Leu Thr Thr Met His Ile Asn Lys Glu Ala Met
290                 295                 300

Gly Glu Arg Ala Val Lys Lys Leu Ile Glu Lys Met Asn Gly Gln Glu
305                 310                 315                 320

Ser Met Asp Glu Lys Ile Val Leu Pro Val Thr Leu Ile Glu Arg Gln
                325                 330                 335

Ser Val Lys Arg Ile Gly
            340
```

<210> SEQ ID NO 33
<211> LENGTH: 353
<212> TYPE: PRT
<213> ORGANISM: C. thermocellum

<400> SEQUENCE: 33

```
Met Asn Ser Lys Asp Ile Ala Lys Ile Val Gly Val Ser Arg Ser Thr
  1               5                  10                  15
```

Val Ser Arg Val Ile Asn Asn Tyr Pro Asp Ile Pro Gln Ala Thr Arg
            20                  25                  30

Glu Lys Val Leu Lys Ala Ile Lys Glu Tyr Asn Tyr Pro Asn Ala
        35                  40                  45

Ser Ala Arg Arg Leu Ala Gly Met Lys Ser Ser Thr Leu Gly Ile Phe
 50                  55                  60

Ile Ile Asp Ile Lys Asp Asn Glu Lys Pro His His Val Ile Glu Asn
 65                  70                  75                  80

Asn Glu Asp Leu Leu Tyr Gly Asn Ser Tyr Phe Ser Pro Phe Ile Asn
            85                  90                  95

Ala Phe Ile Asp Gln Ser Asn Lys Ala Gln Tyr His Val Leu Val Ser
                100                 105                 110

Thr Ile Tyr Ser Ser Asp Glu Leu Trp Lys Ile Gln Ser Ala Phe Tyr
            115                 120                 125

Glu Lys Arg Ile Asp Gly Ala Val Ile Gly Ser Ser Ile Asp
                130                 135                 140

Tyr Ser Lys Ile Phe Glu Ile Met Asp Lys Asp Ser Ile Thr Val Ala
145                 150                 155                 160

Val Asp Leu Asp Met Glu Lys Glu Asn Thr Gly Thr Val Met Ser Val
                165                 170                 175

Asn Ile Asn Asn Tyr Gly Gly Val Ser Asp Ala Ile Asp Tyr Leu Val
            180                 185                 190

Glu Leu Gly His Lys Asp Ile Ala Val Ile Thr Gly Asp Leu Asn Lys
                195                 200                 205

Leu Ser Gly Lys Ile Arg Phe Glu Ser Phe Lys Asp Ala Leu Leu Arg
210                 215                 220

His Gly Leu Pro Leu Asn Asn Asp Phe Ile Ala Tyr Gly Asp Phe Thr
225                 230                 235                 240

Glu Asn Ser Gly Tyr Glu Gly Met Lys Lys Ile Leu Ala Ser Gly Lys
                245                 250                 255

Lys Pro Thr Ala Val Phe Thr Ser Asn Asp Thr Met Ala Ile Gly Ala
                260                 265                 270

Tyr Arg Ala Ile Lys Glu Tyr Gly Leu Lys Ile Pro Glu Asp Ile Ser
            275                 280                 285

Val Met Gly Phe Asp Asn Ser Tyr Ile Ser Gln Tyr Met Ser Pro Pro
290                 295                 300

Leu Thr Thr Val Asn Val Ser Leu Pro Glu Ile Ala Lys Cys Ser Ile
305                 310                 315                 320

Glu Leu Leu Leu Asp Ser Ile Asn Asn Lys Glu Ile Lys Asn Arg Gln
                325                 330                 335

Lys Thr Val Asn Val Gln Ile Val Lys Arg Asn Ser Cys Lys Lys Ile
            340                 345                 350

Val

<210> SEQ ID NO 34
<211> LENGTH: 340
<212> TYPE: PRT
<213> ORGANISM: T. fusca

<400> SEQUENCE: 34

Met Glu Arg Arg Arg Pro Thr Leu Glu Met Val Ala Ala Leu Ala
 1               5                  10                  15

Gly Val Gly Arg Gly Thr Val Ser Arg Val Ile Asn Gly Ser Asp Gln
            20                  25                  30

-continued

Val Ser Pro Ala Thr Arg Glu Ala Val Lys Arg Ala Ile Lys Glu Leu
         35                  40                  45

Gly Tyr Val Pro Asn Arg Ala Ala Arg Thr Leu Val Thr Arg Arg Thr
 50                  55                  60

Asp Thr Val Ala Leu Val Val Ser Glu Asn Asn Gln Lys Leu Phe Ala
 65                  70                  75                  80

Glu Pro Phe Tyr Ala Gly Ile Val Leu Gly Val Ala Leu Ser
                 85                  90                  95

Glu Arg Gly Phe Gln Phe Val Leu Ala Thr Gly Arg Ser Gly Ile Glu
                100                 105                 110

His Glu Arg Leu Gly Gly Tyr Leu Ala Gly Gln His Val Asp Gly Val
                115                 120                 125

Leu Leu Leu Ser Leu His Arg Asp Asp Pro Leu Pro Gln Met Leu Asp
130                 135                 140

Glu Ala Gly Val Pro Tyr Val Tyr Gly Gly Arg Pro Leu Gly Val Pro
145                 150                 155                 160

Glu Glu Gln Val Ser Tyr Val Asp Ile Asp Asn Ile Gly Gly Gly Arg
                165                 170                 175

Gln Ala Thr Gln Arg Leu Ile Glu Thr Gly His Arg Arg Ile Ala Thr
                180                 185                 190

Ile Ala Gly Pro Gln Asp Met Val Ala Gly Val Glu Arg Leu Gln Gly
                195                 200                 205

Tyr Arg Glu Ala Leu Leu Ala Ala Gly Met Glu Tyr Asp Glu Thr Leu
    210                 215                 220

Val Ser Tyr Gly Asp Phe Thr Tyr Asp Ser Gly Val Ala Ala Met Arg
225                 230                 235                 240

Glu Leu Leu Asp Arg Ala Pro Asp Val Asp Ala Val Phe Ala Ala Ser
                245                 250                 255

Asp Leu Met Gly Leu Ala Ala Leu Arg Val Leu Arg Ala Ser Gly Arg
                260                 265                 270

Arg Val Pro Glu Asp Val Ala Val Gly Tyr Asp Asp Ser Thr Val
                275                 280                 285

Ala Glu His Ala Glu Pro Pro Met Thr Ser Val Asn Gln Pro Thr Glu
    290                 295                 300

Leu Met Gly Arg Glu Met Ala Arg Leu Leu Val Asp Arg Ile Thr Gly
305                 310                 315                 320

Glu Thr Thr Glu Pro Val Arg Leu Val Leu Glu Thr His Leu Met Val
                325                 330                 335

Arg Glu Ser Gly
        340

<210> SEQ ID NO 35
<211> LENGTH: 360
<212> TYPE: PRT
<213> ORGANISM: E. coli

<400> SEQUENCE: 35

Met Lys Pro Val Thr Leu Tyr Asp Val Ala Glu Tyr Ala Gly Val Ser
  1               5                  10                  15

Tyr Gln Thr Val Ser Arg Val Val Asn Gln Ala Ser His Val Ser Ala
                 20                  25                  30

Lys Thr Arg Glu Lys Val Glu Ala Ala Met Ala Glu Leu Asn Tyr Ile
             35                  40                  45

Pro Asn Arg Val Ala Gln Gln Leu Ala Gly Lys Gln Ser Leu Leu Ile
 50                  55                  60

```
Gly Val Ala Thr Ser Ser Leu Ala Leu His Ala Pro Ser Gln Ile Val
 65                  70                  75                  80

Ala Ala Ile Lys Ser Arg Ala Asp Gln Leu Gly Ala Ser Val Val Val
                 85                  90                  95

Ser Met Val Glu Arg Ser Gly Val Glu Ala Cys Lys Ala Ala Val His
            100                 105                 110

Asn Leu Leu Ala Gln Arg Val Ser Gly Leu Ile Ile Asn Tyr Pro Leu
        115                 120                 125

Asp Asp Gln Asp Ala Ile Ala Val Glu Ala Ala Cys Thr Asn Val Pro
    130                 135                 140

Ala Leu Phe Leu Asp Val Ser Asp Gln Thr Pro Ile Asn Ser Ile Ile
145                 150                 155                 160

Phe Ser His Glu Asp Gly Thr Arg Leu Gly Val Glu His Leu Val Ala
                165                 170                 175

Leu Gly His Gln Gln Ile Ala Leu Leu Ala Gly Pro Leu Ser Ser Val
            180                 185                 190

Ser Ala Arg Leu Arg Leu Ala Gly Trp His Lys Tyr Leu Thr Arg Asn
        195                 200                 205

Gln Ile Gln Pro Ile Ala Glu Arg Glu Gly Asp Trp Ser Ala Met Ser
    210                 215                 220

Gly Phe Gln Gln Thr Met Gln Met Leu Asn Glu Gly Ile Val Pro Thr
225                 230                 235                 240

Ala Met Leu Val Ala Asn Asp Gln Met Ala Leu Gly Ala Met Arg Ala
                245                 250                 255

Ile Thr Glu Ser Gly Leu Arg Val Gly Ala Asp Ile Ser Val Val Gly
            260                 265                 270

Tyr Asp Asp Thr Glu Asp Ser Ser Cys Tyr Ile Pro Pro Leu Thr Thr
        275                 280                 285

Ile Lys Gln Asp Phe Arg Leu Leu Gly Gln Thr Ser Val Asp Arg Leu
    290                 295                 300

Leu Gln Leu Ser Gln Gly Gln Ala Val Lys Gly Asn Gln Leu Leu Pro
305                 310                 315                 320

Val Ser Leu Val Lys Arg Lys Thr Thr Leu Ala Pro Asn Thr Gln Thr
                325                 330                 335

Ala Ser Pro Arg Ala Leu Ala Asp Ser Leu Met Gln Leu Ala Arg Gln
            340                 345                 350

Val Ser Arg Leu Glu Ser Gly Gln
        355                 360

<210> SEQ ID NO 36
<211> LENGTH: 18
<212> TYPE: DNA
<213> ORGANISM: C. thermocellum

<400> SEQUENCE: 36
aatgaacgcg cgtacatt                                                  18

<210> SEQ ID NO 37
<211> LENGTH: 9
<212> TYPE: DNA
<213> ORGANISM: C. thermocellum

<400> SEQUENCE: 37 aatgaacgc                                                             9

<210> SEQ ID NO 38
<211> LENGTH: 7
```

```
<212> TYPE: DNA
<213> ORGANISM: T. fusca

<400> SEQUENCE: 38 tgggagc                                                              7

<210> SEQ ID NO 39
<211> LENGTH: 8
<212> TYPE: DNA
<213> ORGANISM: E. coli

<400> SEQUENCE: 39 ttgtgagc                                                             8

<210> SEQ ID NO 40
<211> LENGTH: 7
<212> TYPE: DNA
<213> ORGANISM: B. subtillis

<400> SEQUENCE: 40 tgtaagc                                                              7

<210> SEQ ID NO 41
<211> LENGTH: 8
<212> TYPE: DNA
<213> ORGANISM: E. coli
<220> FEATURE:
<221> NAME/KEY: unsure
<222> LOCATION: (7)
<223> OTHER INFORMATION: N at position 7 is either a, t, c, or g

<400> SEQUENCE: 41 gtgkaanc                                                             8

<210> SEQ ID NO 42
<211> LENGTH: 8
<212> TYPE: DNA
<213> ORGANISM: E. coli
<220> FEATURE:
<221> NAME/KEY: unsure
<222> LOCATION: (7)
<223> OTHER INFORMATION: N at position 7 is either a, t, c, or g

<400> SEQUENCE: 42 gtgkaanc                                                             8
```

PROMOTERS AND PROTEINS FROM *CLOSTRIDIUM THERMOCELLUM* AND USES THEREOF

This application claims benefit of U.S. Provisional Patent Application Ser. Nos. 60/626,686, filed Nov. 10, 2004, and 60/626,661, filed Nov. 10, 2004, which are hereby incorporated by reference in their entirety.

This invention was developed with governmental support under U.S. Department of Energy Contract No. DE-FG02-94ER20155. The U.S. Government may have certain rights in this invention.

FIELD OF THE INVENTION

The present invention relates to nucleic acid promoters and proteins isolated from *C. thermocellum* associated with cellulase synthesis, and uses thereof.

BACKGROUND OF THE INVENTION

Of all the energy sources available to mankind today, the most plentiful and probably most under-utilized is the energy from the sun that is converted by plants via photosynthesis and stored as a carbon source. (Demain et al., "Cellulase, Clostridia and Ethanol," *Micro Mol Biol Rev* 69(1):124-154 (2005)). On a worldwide basis, terrestrial plants produce $1.3 \times 10^3$ metric tons (dry weight basis) of wood, which is equivalent to $7 \times 10^9$ metric tons of coal, or about two-thirds of the world's energy requirement. (Demain et al., "Cellulase, Clostridia and Ethanol," *Micro Mol Biol Rev* 69(1):124-154 (2005)). Available cellulosic feedstocks from agriculture and other sources are about 180 million tons per year (Lynd, et al., Bioenergy: Background, Potential, and Policy, *Senate Agricultural Hearings* (2003)). Furthermore, tremendous amounts of cellulose are available as municipal and industrial wastes which today contribute to pollution problems. Thus, great interest exists in the use of cellulosic biomass as a renewable source of energy via breakdown to sugars that can then be converted to liquid fuel. (Demain et al., "Cellulase, Clostridia and Ethanol," *Micro Mol Biol Rev* 69(1):124-154 (2005)).

The *C. thermocellum* cellulosome is a very large cellulase aggregate with a total molecular weight of millions and capable of degrading crystalline cellulose efficiently. Ever since the cellulosomal structure was discovered, it has been recognized that its activity is governed by its unique quaternary structure. The core of the cellulosome is a 250-kDa non-catalytic polypeptide, CipA, which binds to cellulose and serves as a scaffold for the catalytic subunits. CipA contains a series of nine highly homologous domains, termed the cohesin, which serve as receptors for the catalytic subunits. Binding to the cohesin domain is mediated by a highly conserved duplicated sequence of 22 amino acid residues, called the dockerin, which is mostly found at the C-terminus of each cellulosomal catalytic subunit. More than sixty subunits, mostly glycosyl hydrolases, have been found to contain the dockerin. These subunits include endoglucanases, exoglucanases, xylanases, and other hemicellulases. CipA further contains a cellulose-binding domain (CBD), which anchors the array of catalytic components to the cellulose surface.

A particularly attractive solution to the problem of excess waste and the need for alternative energy sources is the conversion of lignocellulosic biomass into motor fuel, i.e. ethanol, by a co-culture of thermophilic, anaerobic microorganisms, for example, a co-culture consisting of a cellulolytic strain such as *C. thermocellum* and a saccharolytic strain, such as *C. thermosaccharolyticum*. Together, these strains attack cellulose and hemicellulose and convert the sugars produced to ethanol. (Demain et al., "Cellulase, Clostridia and Ethanol," *Micro Mol Biol Rev* 69(1):124-154 (2005)). Useful reviews on the biological conversion of lignocellulosic biomass to ethanol have been published. (Lee, J., "Biological Conversion of Lignocellulosic Biomass to Ethanol," *J Biotechnol* 56:1-24 (1997); Lynd, L. R., "Large-Scale Fuel Ethanol From Lignocellulose. Potential, Economics, and Research Priorities," *App. Biochem Biotechnol* 24, 25:695-719 (1990); Lynd, L. R., "Overview and Evaluation of Fuel Ethanol From Cellulosic Biomass: Technology, Economics, the Environment, and Policy," *Annu Rev Energy Environ* 21:403-465 (1996); Lynd, L. R., "Production of Ethanol From Lignocellulosic Material Using Thermophilic Bacteria: Critical Evaluation of Potential and Review," *Adv Biochem Eng/Biotechnol* 38:1-52 (1989); Lynd et al., "Fuel Ethanol from Cellulosic Biomass," *Science* 251:1318-1323 (1991); Lynd et al., "Likely Features and Costs of Mature Biomass Ethanol Technology," *Appl Biochem Biotechnol* 57/58:741-761 (1996); Lynd et al., "Microbial Cellulose Utilization: Fundamentals and Biotechnology," *Microbiol Mol Biol Rev* 66:506-577 (2002); Lynd. et al., "Biocommodity Engineering," *Biotechnol Prog* 15:777-793 (1999); Mielenz, J. R., "Ethanol Production From Biomass: Technology and Commercialization Status," *Curr Opin Microbiol* 4:324-329 (2001); Wyman, C. E., "Potential Synergies and Challenges in Refining Cellulosic Biomass to Fuels, Chemicals, and Power," *Biotechnol Prog* 19:254-262 (2003); Wyman et al., "Biotechnology for Production of Fuels, Chemicals, and Materials from Biomass," *Appl Biochem Biotechnol* 39/40:41-59 (1993); Wyman et al., "Ethanol Fundamentals of Production From Renewable Feedstocks and Use as a Transportation Fuel," *Appl Biochem Biotechnol* 24/25:735-753 (1990).)

Attention has focused on anaerobic thermophiles as "ethanologens" for the following reasons: (i) thermophiles are thought to be robust and contain stable enzymes; (ii) anaerobes generally have a low cellular growth yield, hence more of the substrate is converted to ethanol; (iii) thermophilic fermentations are less prone to detrimental effects of contamination; (iv) growth at higher temperatures may facilitate the removal and recovery of volatile products such as ethanol. (Demain et al., "Cellulase, Clostridia and Ethanol," *Micro Mol Biol Rev* 69(1):124-154 (2005)). Also extremely important are the advantages of cellulase production in situ and the high rates of metabolism of cellulose and hemicellulose.

In addition to addressing a pollution problem, the clostridial co-culture system is potentially capable of dramatically increasing the use of ethanol as a major liquid fuel using renewable photosynthetic biomass as feedstock. The major obstacle to an economic process is the production of the side-products, acetate and lactate, which limits conversion yield. In principle, the concept of a thermophilic ethanol fermentation is a very simple one involving a high-temperature fermentation with reduced need for power-consuming cooling and agitation/aeration of reactor vessels and with the four biologically-mediated events involved in ethanol production (cellulase and hemicellulase formation, cellulose and hemicellulose hydrolysis, hexose fermentation, and pentose fermentation) consolidated in a single process step. By combining recombinant DNA technology and metabolic engineering knowledge, drawbacks in the current methodologies of ethanol production may be overcome. However, most studies on the cellulosome have thus far focused on molecular cloning and characterization of the cellulosomal and non-cellulosomal enzymes, as well as the structure-function relationship of the proteins involved in biomass degradation. Little is known about how the biosynthesis of these proteins is regulated. The task of elucidating the regulatory mechanism is obviously complicated by the large number of the genes and proteins involved.

Cellulase synthesis is known to be controlled by transcription regulators. In the fungus *Trichoderma reesei*, a series of activators and repressors have been found to control the levels of cellulase and xylanase. ACEI serves as a repressor (Aro et al., "ACEI of *Trichoderma reesei* is a Repressor of Cellulase and Xylanase Expression," *Appl Environ Microbiol* 69:56-65 (2003)) whereas ACEII (Aro et al., "ACEII, a Novel Transcriptional Activator Involved in Regulation of Cellulase and Xylanase Genes of *Trichoderma reesei*," *Biol Chem* 276: 24309-24314 (2001)) serves as an activator. In addition, CRE1 mediates glucose repression (Aro et al., "ACEI of *Trichoderma reesei* is a Repressor of Cellulase and Xylanase Expression," *Appl Environ Microbiol* 69:56-65 (2003); Aro et al., "ACEII, a Novel Transcriptional Activator Involved in Regulation of Cellulase and Xylanase Genes of *Trichoderma reesei*," *Biol Chem* 276:24309-24314 (2001); Saloheimo et al., "Carbohydrases From *Trichoderma reesei* and other Microorganisms," *Royal Society of Chemistry, Cambridge UK* 267-279). The soil bacteria *Thermobifida fusca* (formerly *Thermomonospora fusca*) has six known cellulase genes, celA-celF. A protein that binds to a 14 bp inverted repeat found in the promoter region of each cellulase gene has been isolated (Spiridonov et al., "Characterization and Cloning of celR, a Transcriptional Regulator of Cellulase Genes from *Thermomonospora fusca*," *Biol Chem* 274:13127-13132 (1999)). This protein, called CelR, serves as a repressor. Binding of CelR to its target DNA sequence is specifically inhibited by low concentrations of cellobiose (0.2-0.5 mM). A mutant of CelR with a slightly modified hinge helix protein structure has confirmed many of these results (Spiridonov et al., "A celR Mutation Affecting Transcription of Cellulase Genes in *Thermobifida fusca*," *J Bacteriol* 182:252-255 (2000)). The mutation has been shown to cause weaker DNA binding than the wild type protein. CelR is constitutively expressed with posttranslational modifications affecting its DNA binding activity.

Unlike these microorganisms which produce only free cellulases, *C. thermocellum* produces the cellulosome in addition to free enzymes. A large number of the cellulosome components can be classified into three categories: 1) the scaffolding protein (CipA), 2) the dockerin-containing subunits (such as CelS and many others), and 3) the scaffoldin-anchorage proteins which anchor the cellulosome to the cell surface (such as OlpA, OlpB, and Orf2p). The second category alone comprises more than 60 different genes. The long list of the cellulosomal genes is further complicated by many non-cellulosomal cellulase components produced by this bacterium. The shear number of the genes involved in cellulose degradation suggests that regulation of cellulase biosynthesis in this bacterium is complicated.

Regulation of the cellulosomal cellulase and hemicellulase biosynthesis has been studied in the anaerobe, *C. cellovorans* (Han et al., "Regulation of Expression of Cellulosomal Cellulase and Hemicellulase Genes in *Clostridium Cellulovorans*," *Bacteriol* 185:6067-6075 (2003)). The cellulosomal cellulase and hemicellulase genes are expressed into both monocistronic and polycistronic mRNAs. Transcription starts sites are found 61-233 bp upstream from the first nucleotide of each of the respective translation initiation codons. Some cellulase and hemicellulase genes in this bacterium are coordinately regulated by the carbon source present in the medium (Han et al., "Transcription of *Clostridium Cellulovorans* Cellulosomal Cellulase and Hemicellulase Genes," *Bacteriol* 185:2520-2527 (2003)). Furthermore, a catabolite repression type of mechanism regulates cellulase expression.

In *C. thermocellum*, regulation of CelS, the major component of the cellulosome, has been studied at the protein level using western blot. The results indicate that CelS production is higher on cellulose than cellobiose (Dror et al., "Regulation of the Cellulosomal CelS (cel48A) Gene of *Clostridium thermocellum* is Growth Rate Dependent," *Bacteriol* 185:3042-3048 (2003)). Quantitative RNase protection assay revealed that the level of celS mRNA under carbon or nitrogen limitation in a chemostat is a function of the growth rate, lower rate favoring celS expression. Two major transcriptional start sites are found 145 and 140 bp upstream of the translational start site, respectively. The relative activities of the two promoters remain constant under the expression conditions. Similar experiments have been done with the scaffoldin-related genes of the bacterium (Dror et al., "Regulation of Expression of Scaffoldin-Related Genes in *Clostridium thermocellum*," *Bacteriol* 185:5109-5116 (2003)). The transcription levels of cipA, olpB, and orf2A vary with the growth rate under nitrogen or carbon limitation. On the other hand, expression of sdbA is independent from the growth rate. Two transcription start sites have been found 81 and 50 bp upstream of the CipA translational start site, respectively. Transcription from the first promoter ($\sigma^L$-like) occurs under all growth conditions, whereas expression from the second promoter (sA-like) occurs only under carbon limitation.

Identification and characterization of transcription regulators is an important step in understanding the control of cellulase biosynthesis in bacterium, however, no regulators of cellulase synthesis are heretofore identified. What is needed now is identification and characterization of specific transcription regulators of cellulose and hemicellulose synthesis by thermophilic anaerobic microorganisms. Armed with an understanding of transcription regulation of cellulase and hemicellulase synthesis by anaerobes such as *Clostridium* spp., recombinant technology can be partnered with metabolic engineering techniques to develop practical and far-reaching solutions to the problems of excess cellulosic waste and the need for alternative energy sources through the efficient conversion of cellulosic biomass to ethanol.

The present invention is directed to overcoming these and other deficiencies in the art.

SUMMARY OF THE INVENTION

A first aspect of the present invention relates to an isolated nucleic acid promoter suitable for directing expression of a protein or polypeptide encoded by a nucleic acid molecule operably associated with the nucleic acid promoter, where the nucleic acid promoter is isolated from *Clostridium thermocellum*.

A second aspect of the present invention relates to a nucleic acid construct having a nucleic acid promoter, or a fragment thereof, suitable for directing expression of a protein or polypeptide encoded by a nucleic acid molecule operably associated with the nucleic acid promoter, where the nucleic acid promoter is isolated from *Clostridium thermocellum*, a 3' regulatory region; and a cloning site, where the cloning site is between the nucleic acid promoter and the 3' regulatory region.

A third aspect of the present invention is another nucleic acid construct. This nucleic acid construct has the nucleic acid promoter, or a fragment thereof, suitable for directing expression of a protein or polypeptide encoded by a nucleic acid molecule operably associated with the nucleic acid promoter, where the nucleic acid promoter is isolated from *Clostridium thermocellum*, a nucleic acid molecule encoding a protein or polypeptide; and a 3' regulatory region. The nucleic acid promoter, the nucleic acid molecule encoding a protein or polypeptide, and the 3' regulatory region are operably linked to allow expression of the protein or polypeptide.

A fourth aspect of the present invention is yet another nucleic acid construct. This nucleic acid construct includes the nucleic acid promoter, or a fragment thereof, of the present invention, which is suitable for directing expression of a protein or polypeptide encoded by a nucleic acid molecule operably associated with the nucleic acid promoter, where the nucleic acid promoter is isolated from *Clostridium thermocellum*. The construct also includes a nucleic acid molecule encoding a protein and a 3' regulatory region, where the nucleic acid promoter, the nucleic acid molecule encoding a protein or polypeptide, and the 3' regulatory region are operably linked together to allow expression of the protein or polypeptide. Also included are a nucleic acid molecule encoding a repressor protein, a 5' regulatory region, and a 3' regulatory region, where the nucleic acid molecule encoding the repressor protein, the 5' regulatory region and the 3' regulatory region are operably linked together allow expression of the repressor protein.

A fifth aspect of the present invention is a method for directing expression of a protein or polypeptide in a host. This method involves transforming a host with a nucleic acid construct of the present invention, to produce a transformed host, under conditions effective to allow expression of the protein or polypeptide in the host.

A sixth aspect of the present invention is a method for directing in vitro expression of a protein or polypeptide. This method involves providing a cell-free transcription-translation system, providing a nucleic acid template for the cell-free transcription-translation system using a nucleic acid construct according to the fourth aspect of the present invention, and combining the nucleic acid template with the cell-free transcription-translation system under conditions effective to allow expression of the protein or polypeptide in vitro.

A seventh aspect of the present invention is a method for directing inducible in vivo expression of a protein or polypeptide in a host. This method involves transforming a host with the nucleic acid construct according to the fourth aspect of the present invention, above, to produce a transformed host, under conditions effective to allow expression of the protein or polypeptide in the host.

An eighth aspect of the present invention is a method of producing ethanol from a biomass. This method involves providing a host including the nucleic acid construct according to the third aspect of the present invention, contacting a biomass with the host under conditions effective to allow the host to convert the biomass to ethanol, thereby producing ethanol from the biomass.

A ninth aspect of the present invention is an isolated nucleic acid molecule encoding protein or polypeptide, wherein the nucleic acid molecule either: (a) has a nucleotide sequence of SEQ ID NO:5; (b) has at least 90% homology to the nucleic acid sequence of SEQ ID NO:5, (c) hybridizes to the nucleic acid molecule having SEQ ID NO:5 under stringent conditions characterized by hybridization at 62° C. in a buffer comprising 5×SSC, 0.02% ficoll, 0.02% polyvinyl pyrrolidone, 0.02% bovine serum albumin, 2.5 mM NaH$_2$PO$_4$ (pH 7), 0.5% SDS, 2 mM EDTA), and washing conditions include washing filters three times at 65° C., once with 2×SSC, 0.1% SDS, once with 1×SSC, 0.1% SDS and once with 0.5% SSC, 0.1% SDS, or (d) encodes a protein having an amino acid sequence of SEQ ID NO: 6.

A tenth aspect of the present invention is an isolated nucleic acid molecule encoding a repressor protein, where the nucleic acid molecule either: has the nucleotide sequence of SEQ ID NO: 2; has at least 95% homology to the nucleotide sequence of SEQ ID NO:2; hybridizes to the nucleic acid molecule having SEQ ID NO:2 under stringent conditions characterized by hybridization at 62° C. in a buffer comprising 5×SSC, 0.02% ficoll, 0.02% polyvinyl pyrrolidone, 0.02% bovine serum albumin, 2.5 mM NaH$_2$PO$_4$ (pH 7), 0.5% SDS, 2 mM EDTA), and washing conditions include washing filters three times at 65° C., once with 2×SSC, 0.1% SDS, once with 1×SSC, 0.1% SDS and once with 0.5% SSC, 0.1% SDS, or encodes a protein having the amino acid sequence of SEQ ID NO:3.

An eleventh aspect of the present invention is an isolated repressor protein that either: 1) has the amino acid sequence of SEQ ID NO:3, or 2) has at least 95% identity to the amino acid sequence having SEQ ID NO:3.

BRIEF DESCRIPTION OF THE DRAWINGS

FIG. 4 shows 2D gel results of the extracellular proteins produced by *Clostridium thermocellum* grown on cellobiose and on cotton. The intensity and size of the spots indicates how much of each protein is excreted by the cells. The largest protein spots (circled) were subjected to MALDI-TOF analysis (matrix-assisted laser desorption/ionization mass spectroscopy).

FIG. 5 is an amino acid homology of GlyR1(CelR1), GlyR2(CelR2), and GlyR3(CelR3) from *C. thermocellum*; CelR from *T. fusca*; and LacI from *E coli*. FIG. 5 shows the amino acid homology of GlyR1(CelR1) (SEQ ID NO:32), GlyR2(CelR2) (SEQ ID NO:33), and GlyR3(CelR3) (SEQ ID NO:3) from *C. thermocellum*; CelR (SEQ ID NO:34) from *T. fusca*; and LacI (SEQ ID NO:35) from *E. coli*. Boxed regions at the N-terminal end indicate the DNA-binding motif of each protein.

FIG. 7A shows the LacI DNA-binding domain; FIG. 7B shows the GlyR3 DNA-binding domain; FIG. 7C shows the LacI sugar-binding domain; FIG. 7D shows the GlyR3 sugar-binding domain. The DNA-binding domains appear to be highly conserved. In contrast, the sugar-binding domains significantly deviate from each other.

DETAILED DESCRIPTION OF THE INVENTION

Figure 1:
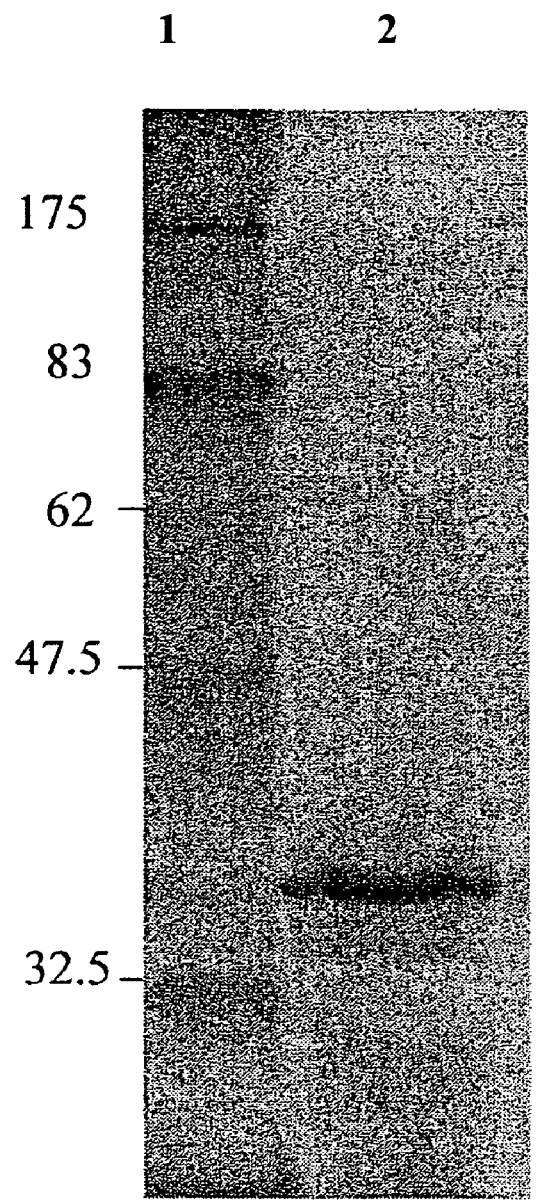
FIG. 1 is a 12% SDS-Polyacrylamide gel electrophoresis of purified rGlyR3 protein, stained with Coomassie Brilliant Blue R-250. Lane 1, Protein molecular weight marker; lane 2, rGlyR3.

Gene regulation and expression is a complex interaction of intracellular and extracellular factors. Genes must be expressed in perfect coordination in order to have organized growth and proper responses to the environment. Cells have several mechanisms to control gene expression, and they can be exerted at transcriptional, post-transcriptional, translational and post-translational levels. However, much of the differential expression can be explained at the transcriptional level when the RNA polymerase III interacts with the DNA and multiple protein factors to initiate the synthesis of mRNA (Roeder, "The Role of Initiation Factors in Transcription by RNA Polymerase II," *Trends in Biochemical Science* 21:327-335 (1996), which is hereby incorporated by reference in its entirety). The region of DNA involved in this pre-transcriptional interaction is called the "promoter." Promoters are usually located next to the 5' end of the coding region of a gene.

In bacterial cells, genes are clustered into operons, i.e., gene clusters that encode the proteins necessary to perform coordinated function, such as biosynthesis of a given amino acid. RNA that is transcribed from a prokaryotic operon is polycistronic, a term implying that multiple proteins are encoded in a single transcript.

In bacteria, control of the rate of transcriptional initiation is the predominant site for control of gene expression. As with the majority of prokaryotic genes, initiation is controlled by two DNA sequence elements that are approximately 35 bases and 10 bases, respectively, upstream of the site of transcriptional initiation and as such are identified as the −35 and −10 positions. These 2 sequence elements are termed promoter sequences, because they promote recognition of transcriptional start sites by RNA polymerase. The consensus sequence for the −35 position is TTGACA, and for the −10 position, TATAAT. (The −10 position is also known as the Pribnow-box.) These promoter sequences are recognized and contacted by RNA polymerase. The activity of RNA polymerase at a given promoter is, in turn, regulated by interaction with accessory proteins, which affect its ability to recognize start sites. These regulatory proteins can act both positively (activators) and negatively (repressors). The accessibility of promoter regions of prokaryotic DNA is, in many cases, regulated by the interaction of proteins with sequences termed operators. The operator region is adjacent to the promoter elements in most operons and in most cases the sequences of the operator bind a repressor protein.

The present invention relates to nucleic acid promoters isolated from *C. thermocellum*. One suitable nucleic acid promoter molecule of the present invention is a promoter isolated from the bacterium *Clostridium thermocellum* and has a nucleic acid sequence corresponding to SEQ ID NO: 1 as follows:

```
aatcaataaa attataacat attacttcaa aagtggggac aaaaaagaac aaaaaaattg    60
aaattttgat gaaaaataca agatatgaat taagtgggcc gaataaaaac tggacagaga   120
agaagaaaac gtgatataat taaattagaa tgaacgcgcg tacattattg aataatccag   180
tgttaaatgg tttcagttta cgatttcaaa tgtttatatc caatttacat ttaaaaacat   240
acaaaacatc aaaagtattt aataccaata tttaaaacac aatatttcag gaggaaaaaa   300
```

This promoter, isolated from *Clostridium thermocellum*, is called hereinafter "the celC promoter." (It was previously known as the celR1 promoter.) It is located at approximately the 300 bp region of DNA upstream from the start codon of the celC gene. The putative ribosome binding site is bolded, above. celC is an inducible promoter, as described in greater detail herein below.

The celC promoter is a part of an operon-like gene cluster consisting of celC, glyR3, and licA, and may also include a possible membrane transporter gene, manB, and celT. Experimental evidence, described in greater detail herein below, indicates that a protein of *C. thermocellum*, GlyR3, exerts negative control by binding to the promoter region of celC.

Thus, another aspect of the present invention is glyR3, a nucleic acid molecule isolated from *C. thermocellum*. glyR3 has a nucleotide sequence corresponding to SEQ ID NO:2, as follows:

```
atgaccagtg aagaaatagc aaaattatgt ggtgtttcca gagccacggt atccagggtt    60
attaacaaca gtcccaacgt aaaagaggaa acgcggcaaa agattctggc agtgataaaa   120
gaaaaaaatt atgttccgat agcgccggca cggcgtttgg ccgggataga cagcaatata   180
attggcctgt ttgttttgga tattgacata tctgagtcaa agtcaaggGt ctcggaaagt   240
acatacttttt cacggctgat aaatctgata atagaccagg caaacaattt tggctttcaa   300
gtattggtgt caattataac ttcacagaaa cagctgagtg aaattagaaa tctcttcatg   360
agcagaacca ttttcagcgg catttttatc ggtgcgttca atgatgaaat ccaacttgat   420
gatgatatta taatgcaaca tcccacaatt attattgacc gccaatcaga aaggatggtg   480
aaaaagccaa acagattggt tgtaaacctg gacaactttg agggtgctta taatgcgaca   540
cagttttttga ttaaattggg gcataccaga attgggcaca tatccgggga ccttagaaaa   600
ctttcgggca tagaacgcta tgaaggatac aaaaaagcat tggaagatgc aggattaggt   660
tttgacaaaa atttggttcg tgaagggaac ttccttgatg acagcggcta taggcttgca   720
cgtgagatat taaaagagaa cgtgacggct atttttctgtg ccaatgatgt aatggcaatt   780
agtgcaatta aagccataaa agaaacgggt ttgagtgtac cggatgatat atctgtaata   840
gggtttgata atacagcaat cggaaattat atcatgcctg cattgacaac tgtgaacgcg   900
ccgttggagc atattgcaga agcatgtatt gagtcattga aatacttttg cgagcacaaa   960
cattttaaac aaaaggaaat cagggttaaa accgatttga taatccggga ttcaaccaag  1020
agggctttgg aattctga                                                1038
```

This nucleic acid molecule encodes the GlyR3 protein, which has an amino acid sequence corresponding to SEQ ID NO:3, as follows:

```
Met Thr Ser Glu Glu Ile Ala Lys Leu Cys Gly Val Ser Arg Ala Thr
 1               5                  10                  15

Val Ser Arg Val Ile Asn Asn Ser Pro Asn Val Lys Glu Glu Thr Arg
                20                  25                  30

Gln Lys Ile Leu Ala Val Ile Lys Glu Lys Asn Tyr Val Pro Ile Ala
            35                  40                  45

Pro Ala Arg Arg Leu Ala Gly Ile Asp Ser Asn Ile Ile Gly Leu Phe
        50                  55                  60

Val Leu Asp Ile Asp Ile Ser Glu Ser Lys Ser Arg Val Ser Glu Ser
65                  70                  75                  80

Thr Tyr Phe Ser Arg Leu Ile Asn Leu Ile Ile Asp Gln Ala Asn Asn
                85                  90                  95

Phe Gly Phe Gln Val Leu Val Ser Ile Ile Thr Ser Gln Lys Gln Leu
                100                 105                 110

Ser Glu Ile Arg Asn Leu Phe Met Ser Arg Thr Ile Phe Ser Gly Ile
            115                 120                 125

Phe Ile Gly Ala Phe Asn Asp Glu Ile Gln Leu Asp Asp Ile Ile
        130                 135                 140
```

| | | | | | | | | | | | | | | | |
|---|---|---|---|---|---|---|---|---|---|---|---|---|---|---|---|
|Met|Gln|His|Pro|Thr|Ile|Ile|Ile|Asp|Arg|Gln|Ser|Glu|Arg|Met|Val|
|145| | | |150| | | |155| | | |160| | | |

| | | | | | | | | | | | | | | | |
|---|---|---|---|---|---|---|---|---|---|---|---|---|---|---|---|
|Lys|Lys|Pro|Asn|Arg|Leu|Val|Val|Asn|Leu|Asp|Asn|Phe|Glu|Gly|Ala|
| | | | |165| | | |170| | | |175| | | |

| | | | | | | | | | | | | | | | |
|---|---|---|---|---|---|---|---|---|---|---|---|---|---|---|---|
|Tyr|Asn|Ala|Thr|Gln|Phe|Leu|Ile|Lys|Leu|Gly|His|Thr|Arg|Ile|Gly|
| | | |180| | | |185| | | |190| | | | |

| | | | | | | | | | | | | | | | |
|---|---|---|---|---|---|---|---|---|---|---|---|---|---|---|---|
|His|Ile|Ser|Gly|Asp|Leu|Arg|Lys|Leu|Ser|Gly|Ile|Glu|Arg|Tyr|Glu|
| | |195| | | |200| | | |205| | | | | |

| | | | | | | | | | | | | | | | |
|---|---|---|---|---|---|---|---|---|---|---|---|---|---|---|---|
|Gly|Tyr|Lys|Lys|Ala|Leu|Glu|Asp|Ala|Gly|Leu|Gly|Phe|Asp|Lys|Asn|
| |210| | | |215| | | |220| | | | | | |

| | | | | | | | | | | | | | | | |
|---|---|---|---|---|---|---|---|---|---|---|---|---|---|---|---|
|Leu|Val|Arg|Glu|Gly|Asn|Phe|Leu|Asp|Asp|Ser|Gly|Tyr|Arg|Leu|Ala|
|225| | | |230| | | |235| | | |240| | | |

| | | | | | | | | | | | | | | | |
|---|---|---|---|---|---|---|---|---|---|---|---|---|---|---|---|
|Arg|Glu|Ile|Leu|Lys|Glu|Asn|Val|Thr|Ala|Ile|Phe|Cys|Ala|Asn|Asp|
| | | |245| | | |250| | | |255| | | | |

| | | | | | | | | | | | | | | | |
|---|---|---|---|---|---|---|---|---|---|---|---|---|---|---|---|
|Val|Met|Ala|Ile|Ser|Ala|Ile|Lys|Ala|Ile|Lys|Glu|Thr|Gly|Leu|Ser|
| | |260| | | |265| | | |270| | | | | |

| | | | | | | | | | | | | | | | |
|---|---|---|---|---|---|---|---|---|---|---|---|---|---|---|---|
|Val|Pro|Asp|Asp|Ile|Ser|Val|Ile|Gly|Phe|Asp|Asn|Thr|Ala|Ile|Gly|
| |275| | | |280| | | |285| | | | | | |

| | | | | | | | | | | | | | | | |
|---|---|---|---|---|---|---|---|---|---|---|---|---|---|---|---|
|Asn|Tyr|Ile|Met|Pro|Ala|Leu|Thr|Thr|Val|Asn|Ala|Pro|Leu|Glu|His|
| |290| | | |295| | | |300| | | | | | |

| | | | | | | | | | | | | | | | |
|---|---|---|---|---|---|---|---|---|---|---|---|---|---|---|---|
|Ile|Ala|Glu|Ala|Cys|Ile|Glu|Ser|Leu|Lys|Tyr|Phe|Cys|Glu|His|Lys|
|305| | | |310| | | |315| | | |320| | | |

| | | | | | | | | | | | | | | | |
|---|---|---|---|---|---|---|---|---|---|---|---|---|---|---|---|
|His|Phe|Lys|Gln|Lys|Glu|Ile|Arg|Val|Lys|Thr|Asp|Leu|Ile|Ile|Arg|
| | | |325| | | |330| | | |335| | | | |

| | | | | | | |
|---|---|---|---|---|---|---|
|Asp|Ser|Thr|Lys|Arg|Ala|Leu|Glu|Phe|
| | |340| | | |345| |

The putative DNA-binding domain of GlyR3 is bolded in SEQ ID NO. 3.

The present invention also relates to a second nucleic acid promoter isolated from *C. thermocellum*. This promoter has a nucleotide sequence corresponding to SEQ ID NO:4, as follows:

```
ttaatatgcc gaccacgttg caattcccgt caaataatgc attttgcagc cgacgaaaca   60
ggcaagataa ctgtattggc tataaatgtt tcaagcagcg gtatattttg cctcccggta  120
aaattaatac aataagctaa aaaactgacg taggataagc aaaacggcgc aatttgagtt  180
gtaacgtaat attttcacta aaaatagtaa ttatttcatg ttgttttttt ttagattaat  240
ttataatata atttattgta taagcaatat cttaattatc attaaagggg gaaaaaaact  300
```

The promoter having a SEQ ID NO:4 was isolated from *Clostridium thermocellum*, and is called hereinafter the "hepp1" promoter. It is located approximately 300 bp upstream from the start codon of the *C. thermocellum* orf 5963 gene. The putative ribosome binding site is bolded, above. The hepp1 promoter is a high efficiency promoter, by which is meant that a protein placed under the control of the hepp1 promoter and introduced into an expression system is expressed at a level that is greater than a protein expressed by a constitutive promoter. As shown in FIG. 4, the expression of a protein under the control of the hepp1 promoter (hepp1 protein, hereinafter), is expressed several fold higher than any other extracellular protein in *C. thermocellum*.

Another aspect of the present invention is a nucleic acid molecule that is controlled by the expression promoter (SEQ ID NO:4) of the present invention in *C. thermocellum*. This nucleic acid molecule has a nucleotide sequence corresponding to SEQ ID NO:5, as follows:

```
atgctcaaga aggtaatcgc attaatgttg gttgctgtta tggctttaag tctggcagca   60
tgtggtggtg gaggaggaaa tactacgact tcaccgcaac caaacgattc ccaaaattcg  120
cctgattcag gaacaaagaa ggacccagta aaattgacca tgtggatcat gcctaacagt  180
```

```
gacacaccgg accaggatct tttgaaagtt gttaagccat tcacagatgc taatcctcat    240
atcacagttg aacctacagt tgttgactgg agtgcagctt tgacaaagat cacagctgct    300
gctacaagtg gtgaagctcc tgacattaca caggttggtt ccacttggac agctgctatc    360
ggtgcaatgg aaggtgcatt ggttgagctt accggaaaaa tcgatacaag tgctttcgtt    420
gaatcaactc tgcagtcagc ttatatcaaa ggcacagaca agatgttcgg tatgccttgg    480
tttactgaaa caagagctct cttctacaga aaagacgctt gcgaaaaagc aggtgtaaat    540
cctgaaacag atttcgcaac ttgggacaaa ttcaaagatg ctctcaagaa actcaacggt    600
attgaagttg acggcaagaa actggttgca ctgggtatgc cgggtaagaa cgactggaac    660
gttgttcata acttctcatg gtggatttac ggtgccggcg gagactttgt aaacgaagaa    720
ggtacacaag ctactttctc aagcgaaaat gctcttaaag gtatcaaatt ctattcagaa    780
cttgctgttg aaggtttgat ggatgagcct tcacttgaaa agaatacaag tgacattgag    840
tccgcatttg gtgacggtgc atacgctact gcattcatgg gtccttgggt tatttcatct    900
tacacaaaga ataagaaga aaacggtaac gaccttatcg acaaaattgg tgttactatg    960
gttcctgaag gacctgcagg aagatatgca ttcatgggtg gaagtaacct tgtaatattc   1020
aactcatcaa agaacaagga tgaagccgtt gaacttctca gttctttgc tagcaaagaa   1080 gctcaggttg aatactcaaa ggttagcaag atgcttccgg ttgttaaagc ggcttacgaa   1140
gatccatact ttgaagattc attgatgaaa gtattcaaag aacaggtaga caaatatggt   1200
aaacactatg catcagttcc tggttgggct tctgcagaag ttatcttctc agaaggtctc   1260
agcaagatct gggataacgt tatggaagtt gatggtgcat acagctacga caagactgta   1320
caaatcgtaa aagatgttga aagtcaaatc aaccaaatat tgcaagaaac aagcaaataa   1380
```

The present invention also relates to the hepp1 protein encoded by the nucleic acid molecule having a nucleotide sequence of SEQ ID NO:5. This protein has an amino acid sequence corresponding to SEQ ID NO:6, as follows:

```
Met Leu Lys Lys Val Ile Ala Leu Met Leu Val Ala Val Met Ala Leu
 1               5                  10                  15

Ser Leu Ala Ala Cys Gly Gly Gly Gly Asn Thr Thr Thr Ser Pro
                20                  25                  30

Gln Pro Asn Asp Ser Gln Asn Ser Pro Asp Ser Gly Thr Lys Lys Asp
                35                  40                  45

Pro Val Lys Leu Thr Met Trp Ile Met Pro Asn Ser Asp Thr Pro Asp
        50                  55                  60

Gln Asp Leu Leu Lys Val Val Lys Pro Phe Thr Asp Ala Asn Pro His
 65                  70                  75                  80

Ile Thr Val Glu Pro Thr Val Val Asp Trp Ser Ala Ala Leu Thr Lys
                85                  90                  95

Ile Thr Ala Ala Thr Ser Gly Glu Ala Pro Asp Ile Thr Gln Val
                100                 105                 110

Gly Ser Thr Trp Thr Ala Ala Ile Gly Ala Met Glu Gly Ala Leu Val
                115                 120                 125

Glu Leu Thr Gly Lys Ile Asp Thr Ser Ala Phe Val Glu Ser Thr Leu
        130                 135                 140

Gln Ser Ala Tyr Ile Lys Gly Thr Asp Lys Met Phe Gly Met Pro Trp
145                 150                 155                 160

Phe Thr Glu Thr Arg Ala Leu Phe Tyr Arg Lys Asp Ala Cys Glu Lys
                165                 170                 175

Ala Gly Val Asn Pro Glu Thr Asp Phe Ala Thr Trp Asp Lys Phe Lys
                180                 185                 190
```

```
Asp Ala Leu Lys Lys Leu Asn Gly Ile Glu Val Asp Gly Lys Lys Leu
        195                 200                 205
Val Ala Leu Gly Met Pro Gly Lys Asn Asp Trp Asn Val Val His Asn
        210                 215                 220
Phe Ser Trp Trp Ile Tyr Gly Ala Gly Gly Asp Phe Val Asn Glu Glu
225                     230                 235                 240
Gly Thr Gln Ala Thr Phe Ser Ser Glu Asn Ala Leu Lys Gly Ile Lys
                245                 250                 255
Phe Tyr Ser Glu Leu Ala Val Glu Gly Leu Met Asp Glu Pro Ser Leu
                260                 265                 270
Glu Lys Asn Thr Ser Asp Ile Glu Ser Ala Phe Gly Asp Gly Ala Tyr
                275                 280                 285
Ala Thr Ala Phe Met Gly Pro Trp Val Ile Ser Ser Tyr Thr Lys Asn
        290                 295                 300
Lys Glu Glu Asn Gly Asn Asp Leu Ile Asp Lys Ile Gly Val Thr Met
305                     310                 315                 320
Val Pro Glu Gly Pro Ala Gly Arg Tyr Ala Phe Met Gly Gly Ser Asn
                325                 330                 335
Leu Val Ile Phe Asn Ser Ser Lys Asn Lys Asp Glu Ala Val Glu Leu
                340                 345                 350
Leu Lys Phe Phe Ala Ser Lys Glu Ala Gln Val Glu Tyr Ser Lys Val
                355                 360                 365
Ser Lys Met Leu Pro Val Val Lys Ala Ala Tyr Glu Asp Pro Tyr Phe
        370                 375                 380
Glu Asp Ser Leu Met Lys Val Phe Lys Glu Gln Val Asp Lys Tyr Gly
385                     390                 395                 400
Lys His Tyr Ala Ser Val Pro Gly Trp Ala Ser Ala Glu Val Ile Phe
                405                 410                 415
Ser Glu Gly Leu Ser Lys Ile Trp Asp Asn Val Met Glu Val Asp Gly
                420                 425                 430
Ala Tyr Ser Tyr Asp Lys Thr Val Gln Ile Val Lys Asp Val Glu Ser
                435                 440                 445
Gln Ile Asn Gln Ile Leu Gln Glu Thr Ser Lys
        450                 455
```

The amino acid sequence of the hepp1 protein has a putative signal peptide (SEQ ID NO:7), shown in bold, above, that allows the protein to be excreted from the cell.

The present invention also relates to other nucleic acid molecules that are variants or fragment of the nucleic acid promoters and the nucleic acid molecules encoding the proteins of the present invention. By "variants" is intended substantially similar sequences. Generally, nucleic acid sequence variants of the invention will have at least 90% identity and alternatively at least 92%, 94%, 96%, 98%, or 99% sequence identity to the native nucleotide sequence. It will be understood by one of skill in the art that the "fragments" will comprise essentially the same functionality as the whole molecule.

As used herein, "sequence identity" or "identity" in the context of two nucleic acid or polypeptide sequences includes reference to the residues in the two sequences that are the same when aligned for maximum correspondence over a specified comparison window. An indication that two peptide sequences are substantially identical is that one peptide is immunologically reactive with antibodies raised against the second peptide. A polypeptide is substantially identical to a second polypeptide, for example, where the two polypeptides differ only by a conservative substitution.

Methods of alignment of sequences for comparison and determination of "sequence identity" are well-known in the art. For purposes of defining the present invention, the BLAST 2.0 suite of programs using default parameters is used. Altschul et al., Nucleic Acids Res. 25:3389-3402 (1997), which is hereby incorporated by reference in its entirety. Software for performing BLAST analyses is publicly available, e.g., through the National Center for Biotechnology Information (USA).

The term "stringent conditions" as used herein refers to parameters which are familiar in the art for hybridizing nucleic acid molecules having high identity. Nucleic acid hybridization parameters may be found in references which compile such methods, e.g. Sambrook, et al Molecular Cloning: A Laboratory Manual, Second Edition, Cold Spring Harbor Laboratory Press, Cold Spring Harbor, N.Y. (1989), or Current Protocols in Molecular Biology, F. M. Ausubel, et al., eds., John Wiley & Sons, Inc., New York, which are hereby incorporated by reference in their entirety As used herein "high stringency" refers to DNA hybridization and wash conditions characterized by high temperature and low salt concentration. More specifically, stringent conditions, as used herein, refers, for example, to hybridization at 56-65° C. in hybridization buffer (4-5×SSC, 0.02% ficoll, 0.02% polyvinyl pyrrolidone, 0.02% bovine serum albumin, 2.5mM NaH2 PO4 (pH 7), 0.5% SDS, 2 mM EDTA). Another stringent hybridization condition is hybridization at 4×SSC at 65° C., followed by a washing in 0.1×SSC at 65° C. for about one hour. Alternatively, an exemplary stringent hybridization condition is in 50% formamide, 4×SSC, at 42° C. Still another example of stringent conditions include hybridization at 62°-65° C. in 6×SSC, 0.05× BLOTTO, and washing at 2×SSC, 0.1% SDS at 62° C. After hybridization, the membrane or other material upon which the DNA is immobilized is washed under condition suitable to remove any non-specifically bound DNA probe. Exemplary washing conditions include washing filters three times at 65° C., once with 2×SSC, 0.1% SDS, once with 1×SSC, 0.1% SDS and once with 0.5% SSC, 0.1% SDS, for 20 min. each. For the purposes of defining the level of stringency, reference can conveniently be made to Sambrook et al., *Molecular Cloning: a Laboratory Manual*, 2nd Edition, Cold Spring Harbor, N.Y., Cold Spring Harbor Laboratory Press, at 11.45 (1989), and Ausubel et al., *Current Protocols in Molecular Biology*, John Wiley & Sons, (1989), which are hereby incorporated by reference in their entirety. The precise conditions for any particular hybridization are left to those skilled in the art because there are variables involved in nucleic acid hybridizations beyond those of the specific nucleic acid molecules to be hybridized that affect the choice of hybridization conditions. These variables include: the substrate used for nucleic acid hybridization (e.g., charged vs. non-charged membrane); the detection method used (e.g., radioactive vs. chemiluminescent); and the source and concentration of the nucleic acid involved in the hybridization. All of these variables are routinely taken into account by those skilled in the art prior to undertaking a nucleic acid hybridization procedure.

Thus, the present invention also encompasses nucleic acid sequences that have at least 90% homology to the nucleic acid sequence of SEQ ID NOs:1, 2, 4, and 5, or that hybridizes to nucleic acid molecules having SEQ ID NOs:1, 2, 4, or 5 under stringent conditions characterized, for example, by hybridization at 62° C. in a buffer comprising 5×SSC, 0.02% ficoll, 0.02% polyvinyl pyrrolidone, 0.02% bovine serum albumin, 2.5mM NaH2 PO4 (pH 7), 0.5% SDS, 2 mM EDTA), and washing conditions include washing filters three times at 65° C., once with 2×SSC, 0.1% SDS, once with 1×SSC, 0.1% SDS and once with 0.5% SSC, 0.1% SDS.

Genetic engineering provides valuable tools for studying promoter activity. By making constructs in which a reporter gene is fused under the control of a promoter sequence, it is possible to observe the specific activity of the promoter by monitoring the expression of the reporter gene (Herrera-Estrella et al., "Chimeric Genes as Dominant Selectable Markers in Plant Cells," *EMBO Journal* 2:987-995 (1983), which is hereby incorporated by reference in its entirety). Gene fusion not only provides a way to eliminate variables associated with post-transcriptional regulation from the experiment but also allows comparisons among different promoters or among variations of the same promoter (promoter deletion analysis).

Thus, the present invention relates to a nucleic acid construct that includes a nucleic acid promoter of the present invention; a nucleic acid molecule encoding a protein or polypeptide, where the nucleic acid molecule encoding the protein or polypeptide is operably linked to the nucleic acid promoter, and a 3' regulatory region operably linked to the nucleic acid molecule, where the 5' and 3' regulatory regions allow expression of the protein or polypeptide that is encoded by the nucleic acid molecule.

Promoter molecules suitable in this aspect of the present invention include nucleic acid promoters derived or isolated from *Clostridium* spp., including *C. thermocellum*, such as those corresponding to SEQ ID NO:1 and NO:4 of the present invention, and variants thereof, as variants are described above.

Nucleic acid molecules encoding a protein or polypeptide that are suitable for making the construct of the present invention include, without limitation, SEQ ID NO:2 and SEQ ID NO:5 of the present invention.

In this and all aspects of the present invention, to "allow" expression means that the nucleic acid construct is prepared with all appropriate elements such that expression of the encoded protein(s) or polypeptide(s) will occur when the conditions for expression are met for a given nucleic acid construct. For example, if the nucleic acid molecule encoding a desired protein or polypeptide is under the control of an inducible promoter, than expression will occur when the inducer is brought into contact with the promoter, in sufficient amounts under conditions appropriate to induce expression. Suitable inducing agents include, without limitation, In this aspect of the present invention, a nucleic acid molecule encoding any desired nucleic acid molecule can be introduced into an expression system or vector of choice using conventional recombinant technology. Generally, this involves inserting the nucleic acid molecule into an expression system to which the molecule is heterologous (i.e., not normally present). The heterologous nucleic acid molecule is inserted into the expression system or vector in proper sense (5'→3') orientation and correct reading frame. Alternatively, a nucleic acid molecule may be inserted in the antisense (3'→5') orientation for use in downregulating or silencing a gene of interest (Fire et al., "Specific Interference by Ingested dsRNA," *Nature* 391:806-811 (1998); (Elbashir et al., "RNA Interference is Mediated by 21- and 22-Nucleotide RNAs," *Gene Dev.* 15(2):188-200 (2001), U.S. Pat. No. 6,204,374 to Sidransky, which are hereby incorporated by reference in their entirety). The vector contains the necessary elements for the transcription and translation of the inserted protein-coding sequences.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Recombinant genes may also be introduced into viruses, such as vaccinia virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference in its entirety), pQE, pIH821, pGEX, pET series (see F. W. Studier et. al., "Use of T7 RNA Polymerase to Direct Expression of Cloned Genes," *Gene Expression Technology* Vol. 185 (1990), which is hereby incorporated by reference in its entirety), and any derivatives thereof. The DNA sequences are cloned into the vector using standard cloning procedures in the art, as described by Sambrook et al., Molecular Cloning: *A Laboratory Manual, Cold Springs Laboratory*, Cold Springs Harbor, N.Y. (1989), or U.S. Pat. No. 4,237,224 to Cohen and Boyer, which are hereby incorporated by reference in their entirety).

A variety of host-vector systems may be utilized to express the desired recombinant protein or polypeptide. Primarily, the vector system must be compatible with the host cell used. Host-vector systems include, but are not limited to, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, retrovirus), insect cell systems infected with virus (e.g., baculovirus); fungi, and plant cells infected by bacteria. The expression elements of these vectors vary in their strength and specificities. Depending upon the host-vector system utilized, any one of a number of suitable transcription and translation elements can be used to carry out this and other aspects of the present invention.

Different genetic signals and processing events control many levels of gene expression (e.g., DNA transcription and messenger RNA ("mRNA") translation). Transcription of DNA is dependent upon the presence of a promoter, which is a DNA sequence that directs the binding of RNA polymerase, and thereby promotes mRNA synthesis. The DNA sequences of eukaryotic promoters differ from those of prokaryotic promoters. Furthermore, eukaryotic promoters and accompanying genetic signals may not be recognized in, or may not function in, a prokaryotic system, and, further, prokaryotic promoters are not recognized and do not function in eukaryotic cells.

Promoters vary in their "strength" (i.e., their ability to promote transcription). For the purposes of expressing a cloned gene, it is desirable to use strong promoters in order to obtain a high level of transcription and, hence, expression of the gene. In some aspects of the present invention, the promoter is the celC promoter of the present invention. This is a bacterial promoter, thus, it is suitable for use in prokaryotic hosts, including, but not limited to *Clostridium* spp., such as *C. thermocellum* and *C. thermosaccharolyticum*, and *E. coli*.

In other aspects of the present invention, the promoter is selected depending upon the host cell system utilized; thus, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls. In the present invention, the nucleic acid molecule encoding the GlyR3 repressor protein (described elsewhere herein) may be included in the nucleic acid construct. In nature, glyR3 may be under the control of the celC promoter, or a portion thereof. Although GlyR3 operates as a repressor of the celC promoter of the present invention, like many such negatively repressed promoters, celC may function at a low level constitutively, driving the expression of GlyR3, which binds to a portion of the celC promoter, thereby allowing only a low level of function, i.e, enough to keep the glyR3 gene expressed in the immediate environment. Thus, incorporating glyR3 in the nucleic acid construct of the present invention provides for control of the timing and level of expression of any other nucleic acid molecule in the construct. Those skilled in the art will understand that the nucleic acid molecule encoding glyR3 can be incorporated be in either the same construct or a separate construct as the construct containing the inducible promoter, or can be a integrated into the host genome. The expression of GlyR3 can be under the direction of an constitutive or inducible or promoter, including, but not limited to, the celC promoter. When expression of the desired protein is appropriate, an inducing agent is added to the environment, in a sufficient amount to overcome the repressor protein, and to allow the promoter of the present invention to express any and all other nucleic acid molecules that are operably bound to the promoter (i.e., under the control, or "driven by" the promoter). When the celC promoter is induced, it is expected to drive a high level of expression of a nucleic acid molecule under its control. "A high level" means a higher measurable level of expression compared to the expression level of the same protein or polypeptide in an organism (expression system) under the control of an endogenous promoter.

In order for the nucleic acid construct to express the desired proteins or polypeptide, appropriate 3' regulatory elements must also be present that allow termination of transcription and proper translation of the protein. For a review on maximizing gene expression see Roberts and Lauer, *Methods in Enzymology*, 68:473 (1979), which is hereby incorporated by reference in its entirety.

Depending on the vector system and host utilized, any number of suitable transcription and/or translation elements, including constitutive, inducible, and repressible promoters, as well as minimal 5' promoter elements may be used. For example, the nucleic acid construct of the present invention can also include a nucleic acid molecule encoding a secretion signal. An exemplary secretion signal of the present invention is the signal leader peptide sequence (SEQ ID NO:7) of the hepp1 protein (SEQ ID NO:6), or a variant thereof. In one aspect of the present invention, portions (fragments) of this protein are used as a fusion protein in an expression system. For example, the signal peptide can be used in the expression system to facilitate excretion of a protein created by the expression promoter. Thus, another aspect of the present invention is a nucleic acid construct in which the nucleic acid molecule encoding the signal peptide sequence is incorporated into a nucleic acid construct in which the hepp1 promoter of the present invention drives the expression of a nucleic acid molecule encoding a protein or polypeptide of choice which is operably linked to the signal peptide. A number of suitable secretion signals are known in the art and others are continually being identified. The secretion signal can be a DNA leader which directs secretion of the subsequently translated protein or polypeptide, or the secretion signal can be an amino terminal peptide sequence that is recognized by a host's secretory pathway. The secretion-signal encoding DNA molecule can be ligated between the promoter and the protein-encoding DNA molecule, using known molecular cloning techniques as described in Sambrook et al., *Molecular Cloning: A Laboratory Manual*, Second Edition, Cold Spring Harbor Press, NY (1989), which is hereby incorporated by reference in its entirety.

In another aspect of the present invention, more than one nucleic acid molecule encoding a protein is included in the nucleic acid construct. In one aspect, two or more nucleic acid molecules encoding a protein are prepared using a single 5' region and a single 3' regulatory region.

In another aspect the construct of the present invention includes more than one nucleic acid molecule under the control of more than one 5' promoter element.

In one aspect of the present invention, a nucleic acid construct includes the nucleic acid promoter, or a fragment thereof, of the present invention, which is suitable for directing expression of a protein or polypeptide encoded by a nucleic acid molecule operably associated with the nucleic acid promoter, where the nucleic acid promoter is isolated from *Clostridium thermocellum*. The construct also includes a nucleic acid molecule encoding a protein and a 3' regulatory region, where the nucleic acid promoter, the nucleic acid molecule encoding a protein or polypeptide, and the 3' regulatory region are operably linked together to allow expression of the protein or polypeptide. Also included are a nucleic acid molecule encoding a repressor protein, a 5' regulatory region, and a 3' regulatory region, where the nucleic acid molecule encoding the repressor protein, the 5' regulatory region and the 3' regulatory region are operably linked together allow expression of the repressor protein.

The present invention also relates to an expression vector including a nucleic acid of the present invention. In this aspect, a nucleic acid molecule encoding a promoter of the present invention, and any additional 5' regulatory molecules desired; one or more nucleic acid molecules encoding a protein or polypeptide of choice, a suitable 3' regulatory region, and if desired, a reporter gene, and/or a marker gene, are incorporated into a vector-expression system of choice to prepare the nucleic acid construct of present invention using standard cloning procedures known in the art, such as described by Sambrook et al., *Molecular Cloning: A Laboratory Manual*, Third Edition, Cold Spring Harbor: Cold Spring Harbor Laboratory Press, New York (2001), which is hereby incorporated by reference in its entirety.

Once the nucleic acid construct of the present invention has been cloned into an expression vector, it is ready to be incorporated into a host cell. Recombinant molecules can be introduced into cells, without limitation, via transformation (if the host cell is a prokaryote), transfection (if the host is a eukaryote), transduction (if the host cell is a virus), conjugation, mobilization, or electroporation, lipofection, protoplast fusion, mobilization, particle bombardment, or electroporation. The DNA sequences are cloned into the host cell using standard cloning procedures known in the art, such as those described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable hosts include, but are not limited to, bacteria, virus, yeast, and fungi.

Accordingly, another aspect of the present invention relates to a method of making a recombinant cell. Basically, this method is carried out by transforming a host cell with a nucleic acid construct of the present invention under conditions effective to yield transcription of the DNA molecule in the host cell. Preferably, a nucleic acid construct containing the nucleic acid molecule(s) of the present invention is stably inserted into the genome of the recombinant host cell as a result of the transformation.

Stable transformants are preferable for the methods of the present invention, which can be achieved by using variations of the methods above as describe in Sambrook et al., *Molecular Cloning: A Laboratory Manual*, Chap. 16, Second Edition, Cold Springs Laboratory, Cold Springs Harbor, N.Y. (1989), which is hereby incorporated by reference in its entirety.

Typically, when a recombinant host is grown for the purpose of producing i.e., expressing, the desired recombinant protein, an antibiotic or other compound useful for selective growth of the transgenic cells only is added as a supplement to the media. The compound to be used will be dictated by the selectable marker element present in the plasmid with which the host cell was transformed. Suitable genes are those which confer resistance to gentamycin, G418, hygromycin, streptomycin, spectinomycin, tetracycline, chloramphenicol, and the like. Similarly, "reporter genes," which encode enzymes providing for production of an identifiable compound identifiable, or other markers which indicate relevant information regarding the outcome of gene delivery, are suitable. For example, various luminescent or phosphorescent reporter genes are also appropriate, such that the presence of the heterologous gene may be ascertained visually. The selection marker employed will depend on the target species and/or host or packaging cell lines compatible with a chosen vector.

The promoter of the present invention can be used in a nucleic acid construct with a protein-encoding nucleic acid molecule which produces a wide variety of proteins. Protein-encoding DNA suitable for use in the present invention include DNA which has been amplified, chemically altered, or otherwise modified. Modification of such protein-encoding DNAs may occur, for example, by treating the DNA with a restriction enzyme to generate a DNA fragment which is capable of being operably linked to the promoter. Modification can also occur by techniques such as site-directed mutagenesis.

The protein-encoding DNA also includes DNA that is completely synthetic, semi-synthetic, or biologically derived, such as DNA derived by reverse transcription from RNA. Such DNA includes, but is not limited to, genes such as those from bacteria, yeasts, animals, or viruses; modified genes, portions of genes, chimeric genes, as well as DNA that encodes for amino acids that are chemical precursors or biologics of commercial value, such as polymers or biopolymers. (Pool et al., "In Search of the Plastic Potato," *Science* 245: 1187-1189 (1989), which is hereby incorporated by reference in its entirety.) Suitable DNA is any DNA for which expression is beneficial to have the DNA expressed under control of an inducible DNA promoter isolated from a bacterial source.

Examples of suitable nucleic acid molecules for use in the present invention include, but are not limited to, that of the present invention having SEQ ID NO:2 and SEQ ID NO: 5, as well as to those encoding therapeutic proteins or polypeptide (e.g., antibodies, cytokines, chemokines), and enzymes. Preferred enzymes are enzymes that are associated with the degradation of cellulosic substrates, and those that are useful in the conversion of cellulosic or other feedstock (referred to generally as "biomass" herein), into ethanol. Such enzymes include, without limitation, cellulase, hemicellulase, endoglucanase, exoglucanase, xylanase, mannanase, pectin lyase, and others.

The present invention also relates to a method of directing the expression a desired protein or polypeptide in vivo, i.e., in a host cell, from which the protein may be recovered. In this aspect of the present invention, the nucleic acid construct having the nucleic acid molecule encoding a desired protein under the control of the promoters of the present invention or a fragment thereof (as described above) is prepared, and when expressed, a recombinant protein is secreted into the growth medium of transgenic host, for example, *Clostridium* spp. To isolate the desired protein, the host cell carrying a recombinant plasmid is propagated, homogenized, and the homogenate is centrifuged to remove bacterial debris. The supernatant is then subjected to sequential ammonium sulfate precipitation. The fraction containing the desired protein of the present invention is subjected to gel filtration in an appropriately sized dextran or polyacrylamide column to separate the proteins. If necessary, the protein fraction may be further purified by HPLC or other chromatography techniques, for example, metal affinity chromatography. Alternative methods known in the art may be used as suitable. In another embodiment of the present invention, the nucleic acid construct is used to prepare a nucleic acid template as needed, for a cell-free translation system. Such in vitro translation systems are well-known by those in the art, including many commercially available systems.

The present invention also relates to method of producing ethanol from a biomass. This method involves, generally, providing a nucleic acid construct of the present invention which has been inserted into a host as described herein above, and is capable of degrading a cellulosic substrate, and contacting a biomass with the host under conditions to allow the host to convert the biomass to ethanol, thereby producing ethanol from the biomass. Expression is "allowed" in those embodiment using an inducible promoter (e.g., celC promoter) by providing a suitable inducing agent, including, without limitation, lichenan, laminarin, laminaribiose, laminaritriose, laminaritriose, laminaripentaose, a 1-3 linkage sugar, a synthetic inducer or any analog thereof to induce expression of the nucleic acid molecule(s) under the control of the inducible promoter.

Suitable constructs include those described above, preferably a construct having the celC or hepp1 promoter of the present invention as at least one of the 5' regulatory regions of the construct, one or more nucleic acid molecules encoding an enzyme that is capable of degrading a cellulosic substrate, and a suitable 3' termination sequence to allow expression of the protein. In one aspect of the present invention the construct also contains the nucleic acid molecule encoding GlyR3.

In another aspect of the present invention, the construct contains, in addition to a nucleic acid molecule encoding a desired protein or polypeptide, a nucleic acid molecule having SEQ ID NO:5, where the nucleic acid molecule having SEQ ID NO:5 is also under control of the promoter of the present invention, thereby creating a fusion protein including the protein having amino acid sequence SEQ ID NO:6, and a second desired protein. Such a construct would particularly useful for the methods of the present invention in which degradation of a cellulosic substrate is involved, e.g., for producing ethanol. Thus, particularly suitable for including in the construct in this aspect is encodes a cellulolytic or saccharolytic enzyme.

Hosts suitable for this and all aspects of the present invention include, without limitation, hosts which are cellulose, hemicellulose, or ethanol producers, where the host is a yeast cell, a fungal cell, or a bacterial cell. Bacterial cells may include, without limitation, any *Clostridium* spp., including *Clostridium thermocellum* and *Clostridium saccharolyticum, Clostridium cellulolyticum, Clostridium acetobutylicum, Clostridium beijerinckii, Clostridium perfringens, Clostridium thermosaccharolyticum*; a *Zymomonas* spp., or *Thermoanaerobacterium saccharolyticum*.

In another aspect of the present invention, the cellulolytic or saccharolytic enzyme is placed under the control of the inducible promoter of the present invention, and glyR3 is placed under control of an other, separately functioning promoter. In this way, expression of the repressor and the other nucleic acid molecules can be controlled individually.

Although many systems have been described for expression of recombinant proteins, including peptides and polypeptides, in microbial systems, most gene expression systems in gram negative bacteria such as *Escherichia coli* have relied exclusively on a limited set of bacterial promoters. The most widely used bacterial promoters have included the lactose [lac] (Yanisch-Perron et al., 1985, *Gene* 33: 103-109), and the tryptophan [trp] (Goeddel et al., 1980, *Nature* (London) 287: 411-416) promoters, and the hybrid promoters derived from these two [tac and trc] (Brosius, 1984, *Gene* 27: 161-172; and Amanna and Brosius, 1985, *Gene* 40: 183-190). Other commonly used bacterial promoters include the phage lambda promoters $P_L$ and $P_R$ (Elvin et al., 1990, *Gene* 37: 123-126), the phage T7 promoter (Tabor and Richardson, 1998, *Proc. Natl. Acad. Sci. U.S.A.* 82: 1074-1078), and the alkaline phosphatase promoter [pho] (Chang et al., 1986, *Gene* 44: 121-125). Each of these promoters has desirable features. However, the ideal promoter for expression of a wide variety of recombinant proteins would offer certain features not found in these commonly used systems. For example, many recombinant products can be toxic to the expression host. Therefore, it is often preferable for the promoter to tightly regulate gene expression during culture propagation when gene expression is undesirable. In contrast, when gene expression is desired, the promoter must be easily controlled and a high expression level is often preferred. The agent or environmental condition that initiates gene expression should be easy to use and ideally of low cost. In general, a tightly regulated system is most desirable. Features of a promoter and general expression system that are most preferred include tightly repressed gene expression in the absence of inducer and highly derepressed gene expression in the presence of inducer. As describe in greater detail elsewhere herein, the celC-GlyR3 inducer/repressor is such a system. Furthermore, when used with cellulolytic strain such as *C. thermocellum* and a saccharolytic strain, such as *C. thermosaccharolyticum*, the promoter of the present invention shows great promise for use in improving current methods of ethanol production and reducing the cost of handling landfill.

EXAMPLES

The following examples are provided to illustrate embodiments of the present invention but are by no means intended to limit its scope.
Materials and Methods
Bacterial Strains and Plasmids

*C. thermocellum* (ATCC 27405) was used as a source for genomic DNA, RNA transcripts, and the for sequencing the GlyR3 protein and identifying the *C. thermocellum* promoters of the present invention. *E. coli* Top 10 (Invitrogen, Carlsbad, Calif.) cells were used as a cloning host for plasmid PTXB1 (New England Biolabs). *E. coli* strain BL21DE3 (Stratagene) was used in expression of recombinant GlyR3.
DNA and Protein Sequence Analyses NCBI BLASTp and BLASTn (1) were used for sequence homology searches. The NCBI conserved domain search protocol (Marchler-Bauer et al., "CDD: A Database of Conserved Domain Alignments With Links to Domain Three-Dimensional Structure," *Nucleic Acids Res* 30:281-283 (2002); Marchler-Bauer, et al., "CDD: A Curated Entrez Database of Conserved Domain Alignments," *Nucleic Acids Res* 31:383-387 (2003)) was used to identity motifs of the putative proteins (Marchler-Bauer et al., "CDD: A Database of Conserved Domain Alignments With Links to Domain Three-Dimensional Structure," *Nucleic Acids Res* 30:281-283 (2002); Marchler-Bauer, et al., "CDD: A Curated Entrez Database of Conserved Domain Alignments," *Nucleic Acids Res* 31:383-387 (2003)). For promoter identification, consensus sequence known to be common in transcription regulator were used to screen the *C. thermocellum* genomic library.

Protein 3-D Structure Modeling

GlyR3 and LacI 3D structure models were created using SWISS-MODEL and the Swiss-PDBViewer (Guex et al., "SWISS-MODEL and the Swiss-PdbViewer: An Environment For Comparative Protein Modeling," *Electrophoresis* 18:2714-2723 (1997)).

Growth Conditions for Organisms

*C. thermocellum* was grown in anaerobic flasks or in hungate tubes with chemically defined MJ medium (Johnson et al., "Chemically Defined Minimal Medium for Growth of the Anaerobic Cellulolytic Thermophile *Clostridium thermocellum*," *Appl Environ Microbiol* 43:1125-1132 (1981), which is hereby incorporated by reference in its entirety). Various carbon sources (cellobiose, lichenan, laminarin, laminaribiose, cotton) were each used at 0.5% of the culture volume. Seed cultures were all grown on cellobiose. After inoculation the cultures were incubated at 60° C. until an appropriated time for each experiment (see figure legends).

*E. coli* strains containing recombinant plasmids were grown in a shaker or on agar plates containing Luria-Bertani medium supplemented with 0.1 mg/ml ampicillin. Isopropylthiogalactoside (IPTG) (50 mM) was added to the medium to induce expression of rGlyR3 when appropriate.

Determination of Protein Concentration

The Bradford Reagent (Bio-Rad, Hercules, Calif.) was used to determine protein concentration using bovine serum albumin (Sigma, St. Louis, Mo.) as a standard.

Electrophoresis Mobility Shift Assay

Gel Shift, or Band Shift Assay, or Electrophoretic Mobility Shift Assay (EMSA) is a technique for studying gene regulation and determining protein:DNA interactions. The assay is based on the observation that complexes of protein and DNA migrate through a non-denaturing polyacrylamide gel more slowly than free DNA fragments or double-stranded oligonucleotides. The gel shift assay is carried out by first incubating a protein(s) (such as nuclear or cell extract) with a $32^P$ end-labeled DNA fragment containing the putative protein binding site. The reaction products are then analyzed on a non-denaturing polyacrylamide gel. The specificity of the DNA-binding protein for the putative binding site is established by competition experiments using DNA fragments or oligonucleotides containing a binding site for the protein of interest or other unrelated DNA sequences.

All EMSA experiments described herein were performed using a 4% polyacrylamide gel and Tris-Borate-EDTA buffer. EMSA reactions all contained: 500 ng poly (dI-dC), 1× Lightshift EMSA kit binding buffer (Pierce), 1× Lightshift loading dye (Pierce), optimized amounts of DNA probe, protein, and saccharides as specified in figure legends.

EMSA Signal Development

EMSA gels were electroblotted onto Biodyne B membrane (Pall Corporation). Signal development was accomplished using the Lightshift Chemiluminescent EMSA kit protocol (Pierce). Kodak Biomax film captured the luminescence for viewing.

Example 1

Cloning of glyR3 Nucleic Acid Molecule

A set of primers were synthesized (Invitrogen, Carlsbad, Calif.) to amplify the glyR3 gene, as well as, to add EcoRV and XhoI restriction sites for cloning: (SEQ ID NO:8) glyR3-F-EcoRV-GCGCGATATCACCAGTGAAGAAATAG-CAAAATTA; (SEQ ID NO:9) glyR3-R-XhoI-GCGCCTC-GAGGAATTCCAAAGCCCTCTTGGTT Polymerase chain reaction (PCR) was utilized using genomic *C. thermocellum* DNA as a template. Extensor Hi-Fidelity PCR Enzyme (ABgene) was the polymerase of choice due to its ability to accurately amplify longer DNA products. The standard Extensor protocol was followed with the exception of an 80 second PCR extension time. The PCR product was run on a 1% agarose gel with a molecular weight marker to verify the correct size. Next, the PCR product was digested with EcoRV and XhoI. The PTXB 1 plasmid was digested with NruI and XhoI. The products of the digestions were ligated. The ligation product was transformed by electroporation (Bio-Rad, Hercules, Calif. Gene Pulser II) into *E. Coli* TOP10 cells. Cells were plated onto Luria-Bertani agar plates with 0.1 mg/ml ampicillin and incubated at 37° C. for 16 hours. Colonies were picked and plasmid isolated (Promega, Madison, Wis. Wizard Mini-Prep Kit). Restriction digests were used to verify the presence of the insert.

Example 2

Expression and Purification of Recombinant Protein

PTXB 1 containing the glyR3 insert was transformed by electroporation into *E. Coli* BL21DE3. cells. The cells were grown to a density of 0.8 (OD 600), then 50 mM IPTG was added to the culture. After inducing the expression of rGlyR3 with IPTG, the culture was allowed to incubate in a shaker at 37° C. for 4 hours. At 4 hours, the culture was centrifuged at 5,000 g for 5 minutes and the supernatant decanted. The New England Biolabs (NEB) IMPACT system protein purification protocol was followed. The cells were resuspended in column buffer (20 mM HEPES, 500 mM NaCl, and 1 mM EDTA) and then sonicated for cell lysis. The sonicated product was centrifuged and the supernatant was added to chitin beads (NEB) at room temperature for 1 hour. The chitin beads were washed with 200 ml of column buffer at a flow rate of 2 ml/min. Next, the beads were incubated with 100 mM DTT at 4° C. overnight. The resulting flow-through was concentrated using a Microsep 3K (Pall) and checked for size and purity using a 12% SDS-PAGE, as shown in FIG. 1.

Example 3

Creating DNA Probes for EMSA

Probes for EMSA were created using PCR with Thermostart Taq (ABgene) as a polymerase. The standard Thermostart protocol was used with varying extension times (1 kb/minute rule always followed) and different annealing temperatures (57° C.-62° C.). Primers were synthesized with a 5' biotin label by Invitrogen (Carlsbad, Calif.). Primers (5'-3') used:

```
                                            (SEQ ID NO:10)
entire_celCProm-F-biotin:- CCGAATAAAAACTGGACAGAG;

(SEQ ID NO:11)
Entire_celCProm-R-unlab:- TCCTCCTGAAATATTGTGTTTTA (SEQ ID NO:12)
celCProm_1st_100bp-R-unlab:-
TGAAACCATTTAACACTGGATTAT
```

-continued (SEQ ID NO:13) celCProm_2$^{nd}$_100bp-F_biotin-
GTTTACGATTTCAAATGTTTATATC.

For probes that contained just the 18 bp binding site, complementary DNA fragments were synthesized and annealed by heating to 94 C and then cooling:

(SEQ ID NO:14) BS-F-Biotin- AATGAACGCGCGTACATT (SEQ ID NO:15) BS-R-Unlab- AATGTACGCGCGTTCATT

Example 4

Inducibility of Gene Expression in *C. thermocellum*

To test the effect of growth substrate on the inducibility of the expression of celC, glyR3, licA, orf4, manB, and celT genes in *C. thermocellum*, *C. thermocellum* was grown on substrates containing either a 1-4 linked sugar (cellobiose) or a 1-3 linked sugar (laminarin, lichenan, and laminaribiose). RT-qPCR was carried out on the cells to determine the level of 16S transcripts of the genes, as follows.

The bacterium was grown on the substrates for a time course of 50 hrs. Each 10 hrs a sample was taken. Cultures were centrifuged to collect the cells. Everything used from this point forward was RNase free. Trizol (Invitrogen, Carlsbad, Calif.) was added to the cells for lysis. Chloroform was added at ⅕ the volume of Trizol used for lysis. The mixture was allowed to incubate at room temperature for 5 minutes, and centrifuged at maximum speed for 10 minutes at 4° C. The soluble layer of the reaction was decanted to a fresh tube. 500 µl of isopropanol was mixed into the reaction and the tube was centrifuged for 15 minutes at 13,000 rpm and 4° C. The supernatant was removed from the tube and 500 µl of 75% ethanol was used to wash the RNA. The RNA pellet was allowed to dry and was reconstituted with DEPC treated water. The RNA was digested with DNase I, to get rid of any DNA contamination. RNA concentration was measured using a Hitachi U-2000 spectrophotometer at 260/280 nm. Reverse transcriptase reactions were set up for each RNA sample. A standard protocol for MMLV (Invitrogen, Carlsbad, Calif.) was used. 300 ng Random Primers and 200 ng of RNA were in every reaction. After the reverse transcriptase protocol was completed the resulting cDNA was diluted 100× with sterile water.

Bio-Rad (Hercules, Calif.) iQ SYBR Green Supermix was used for qPCR. Each reaction consisted of 1 µl cDNA, 7.5 µl Bio-Rad (Hercules, Calif.) Supermix, 5.75 µl water, and 250 nM of each primer. A Bio-Rad (Hercules, Calif.) iCycler IQ accomplished the real-time PCR. Primers used for qPCR include:

```
(SEQ ID NO:16)  16S-F-AATTCGAAGCAACGCGAAGAAC (SEQ ID NO:17)  16S-R-GCGGGACTTAACCCAACATCTC (SEQ ID NO:18)  celC-F-CGGGAACATATTGCCTTTGAAC (SEQ ID NO:19)  celC-R-GGTGGAATCAATTTCCCTGATTG (SEQ ID NO:20)  glyR3-F-GGGCATAGAACGCTATGAAGGA (SEQ ID NO:21)  glyR3-R-TATAGCCGCTGTCATCAAGGAA (SEQ ID NO:22)  licA-F-TTGACCAAGGTCCGAACAGAA (SEQ ID NO:23)  licA-R-TTCAAACCTGCGCTCATTAACA (SEQ ID NO:24)  orf4-F-TCACTGCTTGATCCTCGTTTGT (SEQ ID NO:25)  orf4-R-ACGCCATTTCTCTTGCAATCTC (SEQ ID NO:26)  manB-F-GGTATCCATAAAGGTGCCCAGA (SEQ ID NO:27)  manB-R-ATTCACCGAAGTGCTTGTACCC (SEQ ID NO:28)  celT-F-TGTGGATTCCCAGAACACCAAC (SEQ ID NO:29)  celT-R-CCTCAGGCAAACCAAACTTCAC
```

Figure 2:
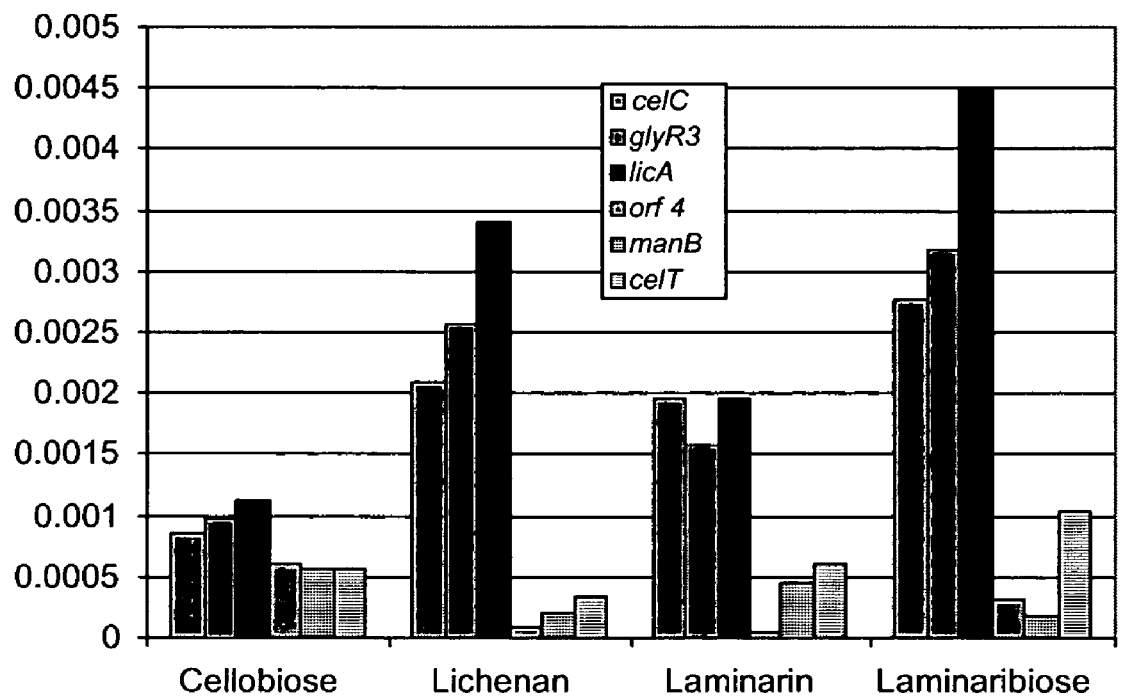
FIG. 2 is a graph showing RT-qPCR results detailing the inducibility of expression of celC, glyR3 and licA when *Clostridium thermocellum* is grown on a 1-3 linked sugar: lichenan, laminarin and laminaribiose, compared to the 1-4 linked sugar, cellobiose. The bacterium was grown on the substrates for a time course of 50 hrs. Each 10 hours a sample was taken and the RNA harvested, DNase I digested, subjected to reverse transcription, and then qPCR. Columns left to right for each substrate represent relative transcription levels of celC, glyR3, licA orf4 manB and celT, respectively. The qPCR levels are all relative to the 16S transcript in *C. thermocellum*.

As shown in FIG. 2, when cellobiose is the substrate, less of the transcript containing the genes is produced. All results are shown for expression of each gene relative to the 16S transcript expression.

Example 5

In Vitro Transcription Assay

Figure 3:
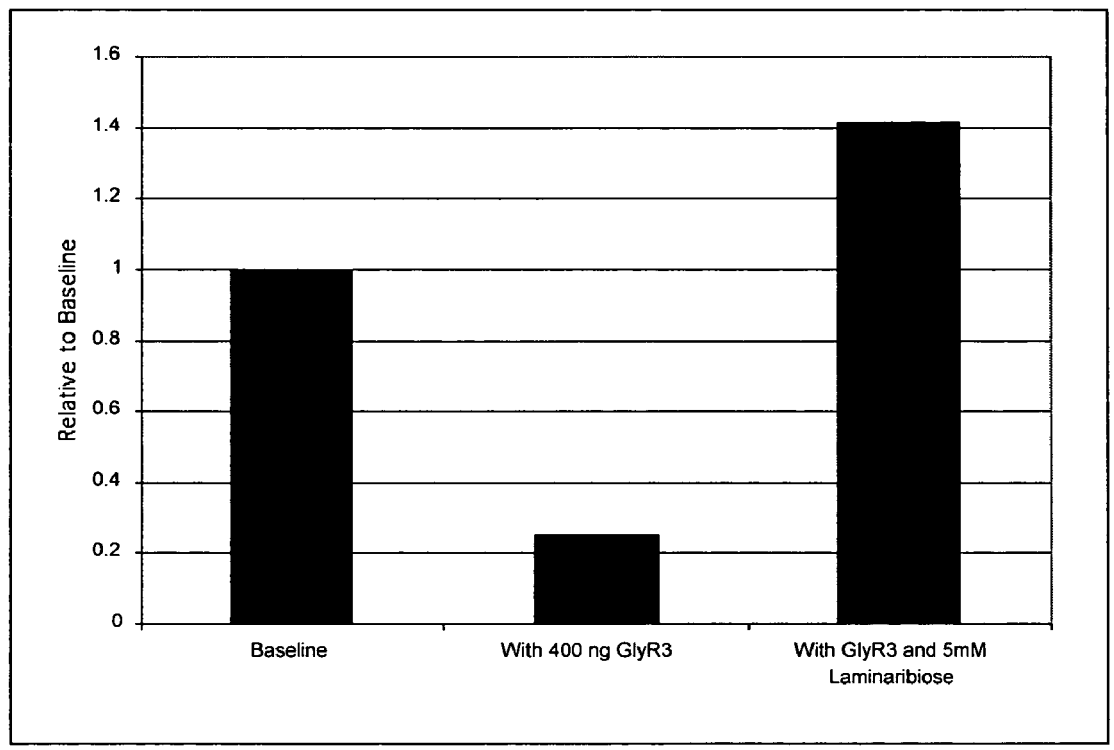
FIG. 3 is RT-qPCR results of an in vitro transcription assay, demonstrating the ability of GlyR3 (400 ng) to inhibit celC transcription, while expression of the transcript was inducible by Laminaribiose. The baseline transcription mixture consists of: rNTPs, transcription buffer, 1 ug of 850 bp DNA containing celC and its promoter region, 10 ul *C. thermocellum* cell lysate (grown on cellobiose). After transcription, the RNA was harvested, DNase I digested, used in a Reverse Transcriptase reaction and then in qPCR.

A DNA template for in vitro transcription was created using the following primers (SEQ ID NO:30): Invt-F-CCGAATAAAAACTGGACAGAAG; (SEQ ID NO:31): Invt-R-CCAGTGGGCTTTCTGATGC) to amplify the 200 bp celC promoter along with 650 bp of the celC gene. PCR used a standard reaction for Extensor Hi-Fidelity Enzyme with genomic DNA as template. Each in vitro transcription assay contained: 10 µl *C. thermocellum* cell lysate (cellobiose grown culture), 2 µl RNase Out (Invitrogen, Carlsbad, Calif.), 1× RNA polymerase buffer, 1 µg of DNA template, 25 nM rNTP's, differing amounts of rGlyR3, differing amounts of laminaribiose, and DEPC water to a volume of 50 µl. The reactions were incubated at 60° C. for 50 minutes. After incubation the resulting RNA was isolated using the previously described Trizol method. The isolated RNA was subjected to DNase I digestion and a standard reverse transcription reaction as described above. Using the qPCR protocol already outlined, with primers for celC, it was possible to show the amount of transcript created for each reaction. As shown in FIG. 3, 400 ng of GlyR3 can inhibit transcription of the celC gene. When 5 mM laminaribiose is added to the transcription mixture, in addition to 400 ng of GlyR3, transcription returned to baseline levels or greater

Example 6 hepp1 Identified by 2-D Gel Analysis

*C. thermocellum* was grown using cellobiose for 30 hours and using cotton for 56 hours. The cells were then centrifuged at 5000 g for 10 minutes. The supernatant was concentrated with a Microsep 3K (Pall) and the protein concentration determined by Bradford Assay. Zoom IPG strips (pH 4-7) (Invitrogen, Carlsbad, Calif.) were used to run the first dimension gel. 10 mg of protein was allowed to rehydrate into the strips as outlined in the standard Zoom IPG manual. Both strips went through IEF focusing on a Scie-plas IEF-SYS unit. The following voltage steps were used for focusing: 175 V for 20 min, 400 V for 20 min, 750 V for 20 min, and 1000 V for 4000 V-hr.

Once focusing was complete, the Zoom IPG strips were loaded to the top of a 10% SDS-PAGE and went through electrophoresis at 120 V. The resulting gels were silver stained (Bio-Rad, Hercules, Calif.) using the typical protocol provided for the reagents. Comparisons between the cellobiose and cotton gel patterns were made. Spots of interest were excised from the gel and sent to the University of Rochester Protein Core Facility where they underwent MALDI-TOF analysis. The hepp1 protein was identified by this analysis. As shown in FIG. 4, the MALDI-TOF analysis mass spec technique allows for the identification of the protein in the spots. The spots that correspond to hepp1 (High Expressing Protein 1) are circled on the 2D gel pictures. As FIG. 4 shows, hepp1 is expressed in large amounts when C. thermocellum is grown on either cellobiose or cotton, indicating that the expression of some extracellular protein in the bacterium is likely under the control of an inducible promoter, and that when induced, the promoter drives a level of protein expression that is significantly higher than the constitutive expression of C. thermocellum extracellular proteins.

Example 7

Identification of LacI-Homologous proteins, GlyR3

BLAST search (Altschul et al., "Basic Local Alignment Search Tool," J Mol Biol 215:403-410 (1990)) against the C. thermocellum genomic sequence for genes that are homologous to lacI yielded three candidate genes. The first gene ORF 3541 (glyR1) encoded a protein (342 amino acids) (SEQ ID NO:32) that is 22% identical and 43% similar to LacI (SEQ ID NO:35). The second gene ORF 7355 (glyR2) encoded a protein (353 amino acids) (SEQ ID NO:33) that is 29% identical and 49% similar to LacI. The third gene ORF 1926 (glyR3) encoded a protein (345 amino acids) (SEQ ID NO:3) that is 27% identical and 49% similar to LacI All of these putative proteins were also homologous to other regulatory proteins involved in carbon-source utilization, such as GalR and CelR (SEQ ID NO:34). FIG. 5 shows the amino acid homology of GlyR1(CelR1), GlyR2(CelR2), and GlyR3 (CelR3) from C. thermocellum; CelR from T. fusca; and LacI from E coli.

Example 8

Motifs of the GlyR Proteins

Figure 6:
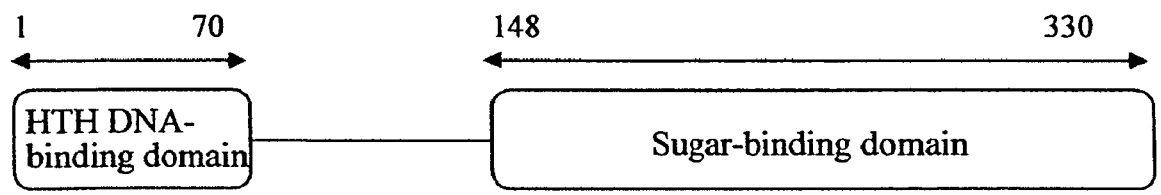
FIG. 6 is a diagram of the domain structure of GlyR3.

NCBI conserved domain search (Marchler-Bauer et al., "CDD: A Database of Conserved Domain Alignments With Links to Domain Three-Dimensional Structure," Nucleic Acids Res 30:281-283 (2002); Marchler-Bauer, et al., "CDD: A Curated Entrez Database of Conserved Domain Alignments," Nucleic Acids Res 31:383-387 (2003)) revealed that each of these putative regulatory proteins contains two major domains. A helix-turn-helix DNA-binding domain is N-terminal to a sugar-binding domain. The domain structure of the GlyR proteins is thus similar to the LacI structure and suggests the repressor role of these proteins. The domain structure of GlyR3 is illustrated in FIG. 6. GlyR1 and GlyR2 have similar domain structures.

Example 9

3-D Structure Modeling of GlyR3

Figure 7:
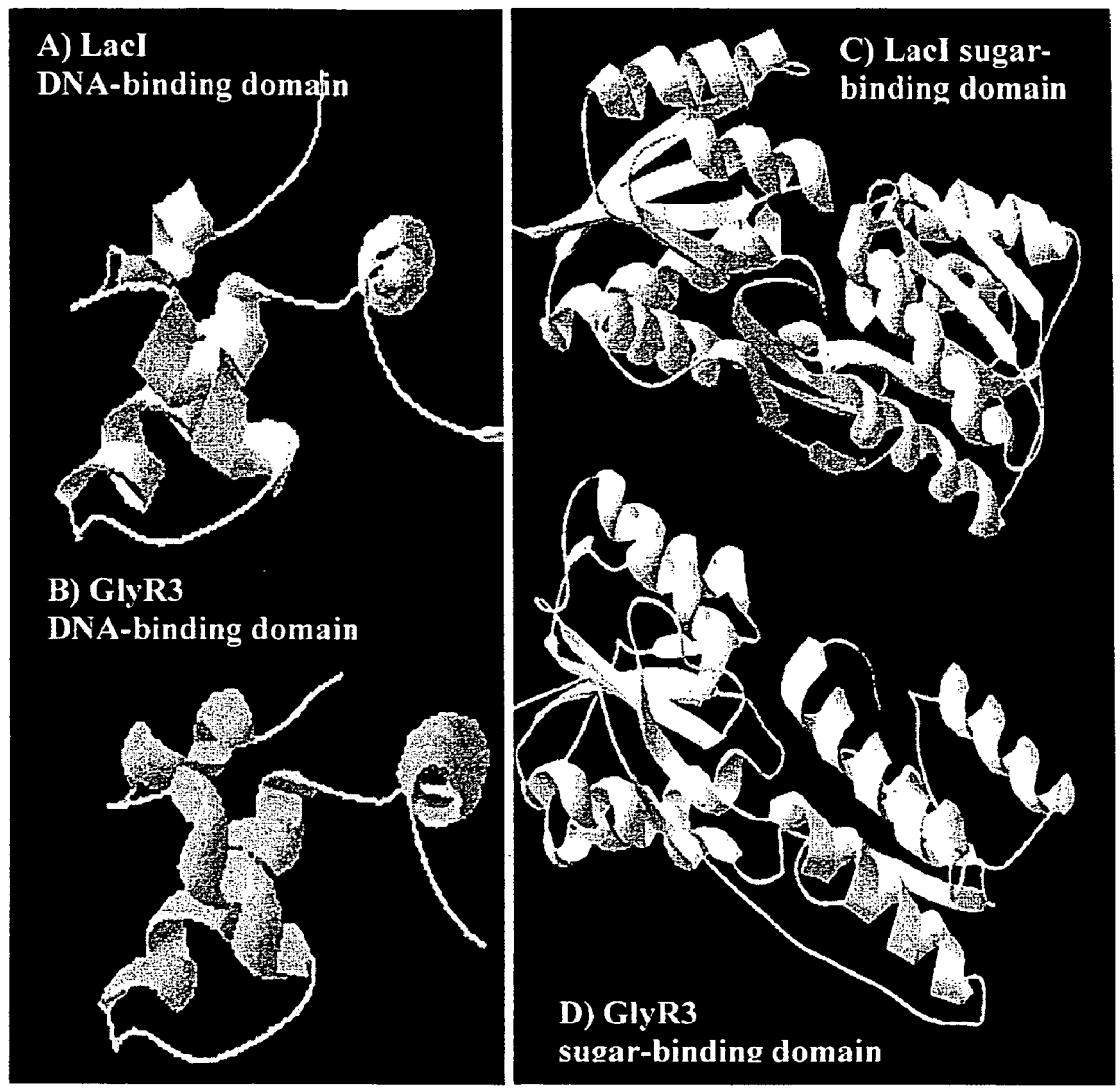
FIGS. 7A-D show the domain structures of GlyR3 modeled after LacI using SWISS-MODEL.

To further analyze the GlyR3 structure, homology modeling of the GlyR3 3-D structure after LacI using SWISS-MODEL and the Swiss-PDBViewer (Guex et al., "SWISS-MODEL and the Swiss-PdbViewer: An Environment For Comparative Protein Modeling," Electrophoresis 18:2714-2723 (1997)) was carried out. The results are shown in FIGS. 7A-B. The DNA-binding domain of GlyR3 shows a helix-turn-helix structure very similar to that of LacI. On the other hand, the folding of the sugar-binding domain of GlyR3 is substantially different from its equivalent in LacI. The results are consistent with the expectation that GlyR3 is a DNA-binding protein regulated by a sugar other than lactose.

Example 10

The Operon-like Gene Cluster Containing glyR3

Figure 8:
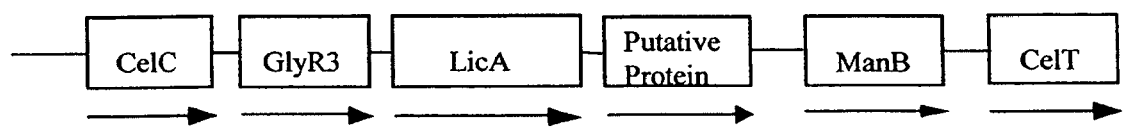
FIG. 8 is a diagram of the operon-like gene cluster in which glyr3 is located. The arrows show direction of transcription.
Figure 9:
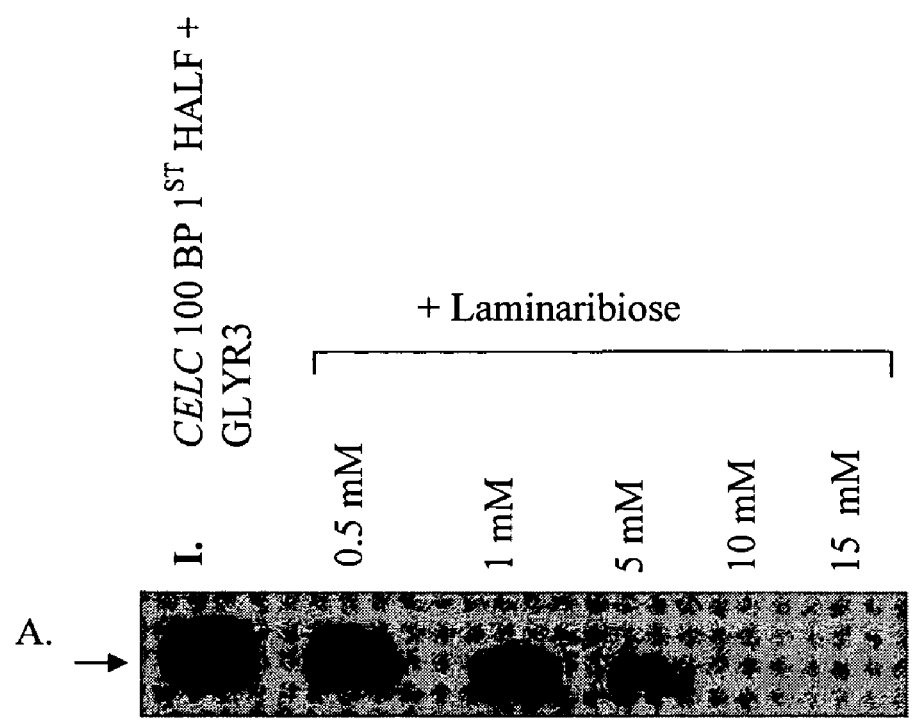
FIG. 9 is a gel showing the results of an EMSA (electrophoretic mobility shift assay). Effect of laminaribiose on the GlyR3 (0.5 ng)-100 bp celC promoter (furthest upstream region) (5 ng) interaction. The DNA-protein complex diminished as the concentration of laminaribiose increased.

Interestingly, glyR3 is located within an operon-like gene cluster (Petre et al., "Purification and Properties of the Endoglucanase C of Clostridium thermocellum Produced in Escherichia Coli," Biochimie 68:687-695 (1986)) including the genes encoding CelC, GlyR3, LicA, a putative membrane protein, ManB, and CelT, respectively, as shown in FIG. 8. CelC (Petre et al., "Purification and Properties of the Endoglucanase C of Clostridium thermocellum Produced in Escherichia Coli," Biochimie 68:687-695 (1986); Schwarz et al., "Nucleotide Sequence of the celC Gene Encoding Endoglucanase C of Clostridium thermocellum," Gene 63:23-30 (1988)) and LicA (Fuchs et al., "Lic16A of Clostridium thermocellum, a Non-Cellulosomal, Highly Complex Endo-Beta-1,3-Glucanase Bound to the Outer Cell Surface," Microbiology 149:1021-1231 (2003)) have been shown to be non-cellulosomal proteins. In contrast, ManB (Kurokawa et al., "Sequence of the Clostridium thermocellum Mannanase Gene man26B and Characterization of the Translated Product," Biosci Biotechnol Biochem 65:548-554 (2001)) and CelT (Kurokawa et al., "Clostridium thermocellum Cellulase CelT, a Family 9 Endoglucanase Without an Ig-Like Domain or Family 3c Carbohydrate-Binding Module," Appl Microbiol Biotechnol 59:455-461 (2002)) are components of the cellulosome, both containing a dockerin domain. The structure of the gene cluster and the homology between GlyR3 and LacI suggest that GlyR3 serves as a repressor of the putative operon. GlyR3 was cloned and expressed in E. coli. As shown in FIG. 9, purified GlyR3 binds to the CelC promoter region, and binding is capable of being inhibited by laminaribiose. Thus, laminaribiose appears to serve as an inducer of the operon by inactivating binding of GlyR3 to the promoter region.

Example 11

GlyR3-celC Promoter Binding in Clostridium thermocellum Extracts

Figure 10:
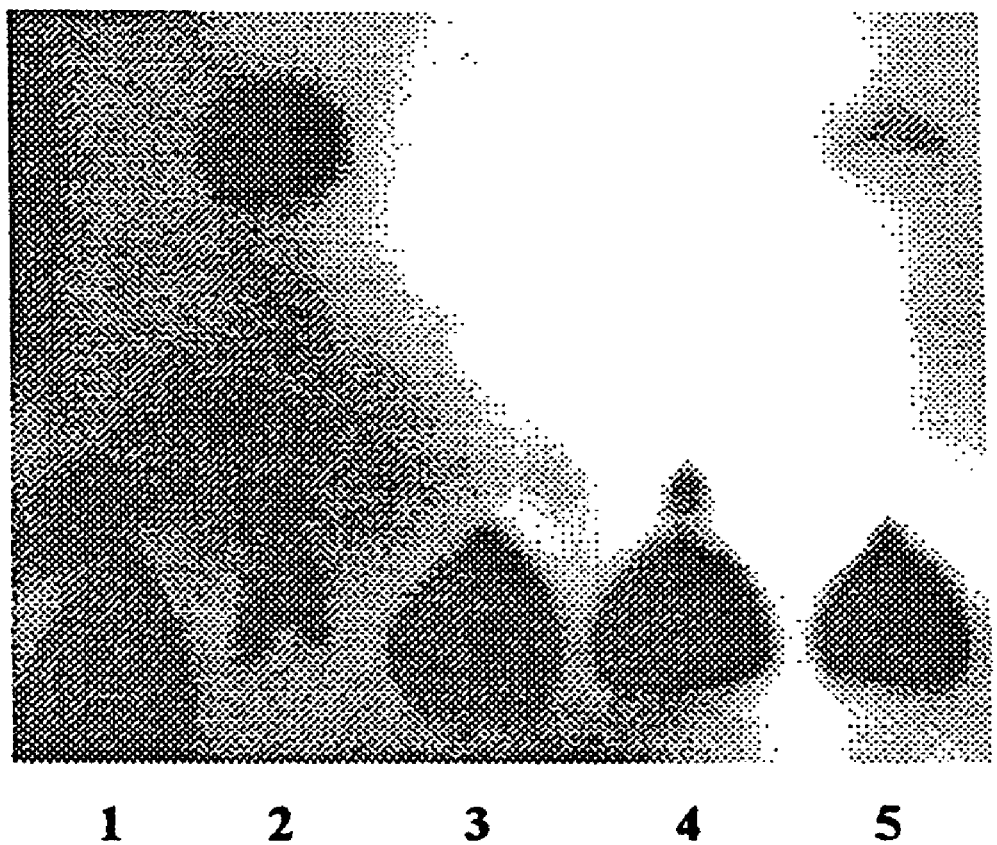
FIG. 10 is a gel showing the results of an EMSA testing the DNA binding activity of *C. thermocellum* extract with celC promoter region. All lanes contain 5 ng of a 100 bp celC promoter region fragment containing the putative binding site. Lane 1, no protein; Lane 2, 1 ng rGlyR3; Lane 3-4, *C. thermocellum* crude extract from cellobiose grown culture (200 ng, 500 ng); Lane 5, *C. thermocellum* crude extract from lichenan grown culture, 120 ng.

C. thermocellum grown on cellobiose as a carbon source failed to show binding to the celC promoter region in EMSA experiments, as shown in FIG. 10, lanes 3-4. However, extracts from lichenan grown cultures show binding activity, shown in FIG. 10, lane 5. The resulting shifted band ran at the same level as rGlyR3, seen in FIG. 10, lane 2. The bandshift was extracted from the EMSA gel and subjected to SDS-PAGE analysis. The resulting protein was used in MALDI-TOF analysis (33% sequence coverage) and was identified as GlyR3.

Example 12

Figure 11:
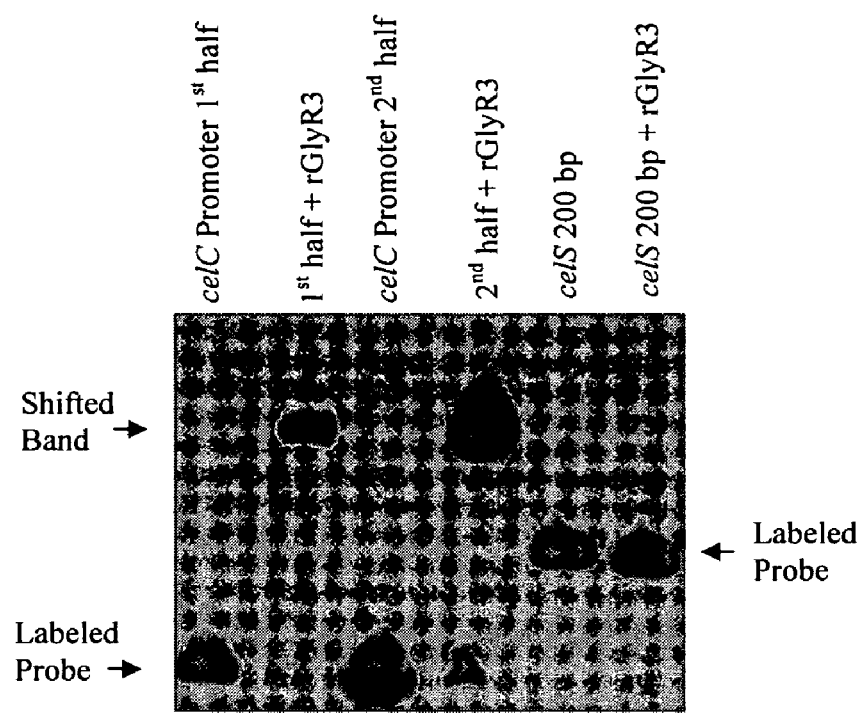
FIG. 11 is a gel showing EMSA result detailing the specific binding of GlyR3 to the celC promoter region. The first and second halves of the celC promoter are used as probes (5 ng each), Lanes 1 and 3, respectively. rGlyR3 (0.5 ng) creates a shifted band with both probes, Lanes 2 and 4, signifying binding to both fragments. A 200 bp fragment of the celS structure gene is used as probe, lanes 5 and 6. No band shift occurs, rGlyR3 does not bind to this DNA fragment.
Figure 12:
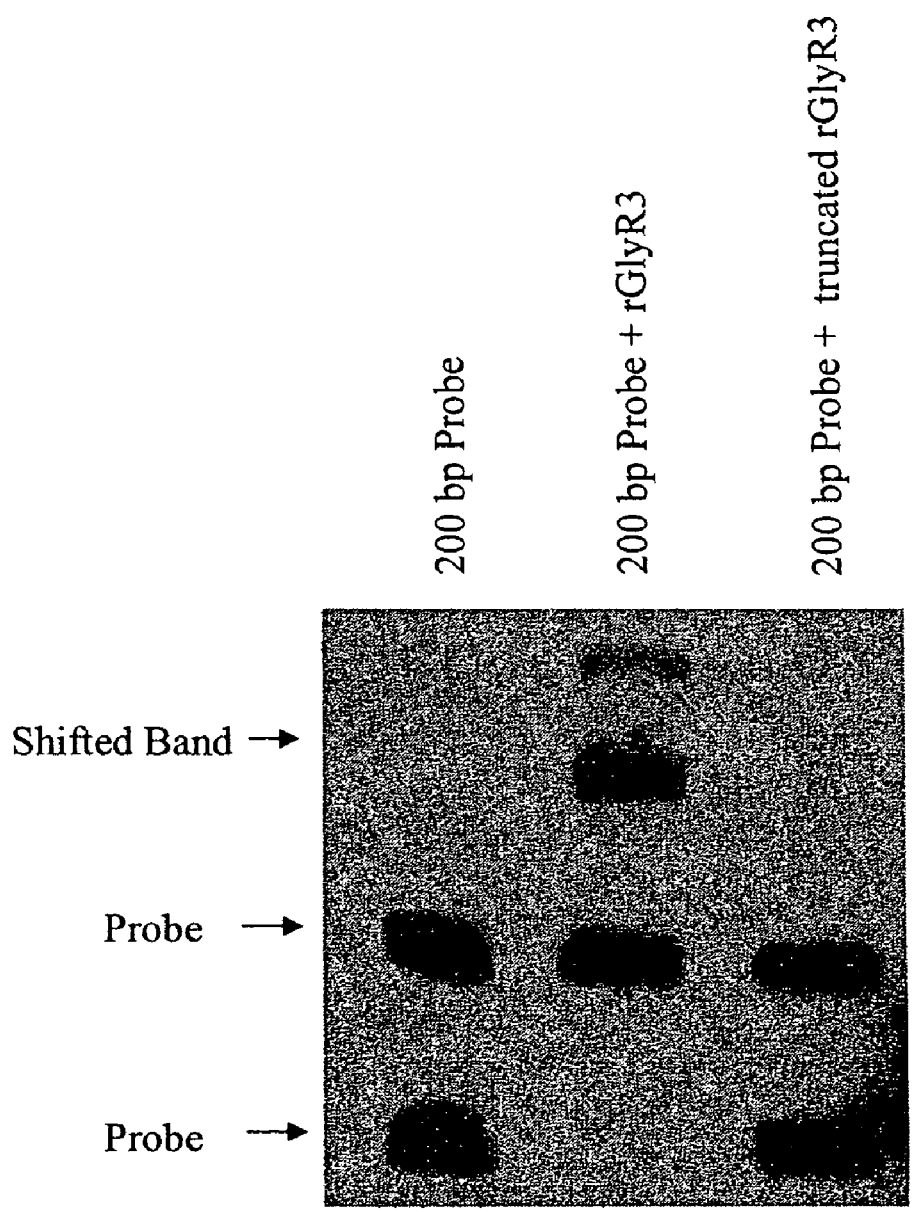
FIG. 12 is a gel showing the results of an EMSA. GlyR3 (1 ng) binds to the 200 bp celC promoter region (5 ng). A truncated version of the GlyR3 protein, that does not contain the N-terminal DNA binding domain, fails to bind to the same promoter region, as shown in FIG. 12.
Figure 13:
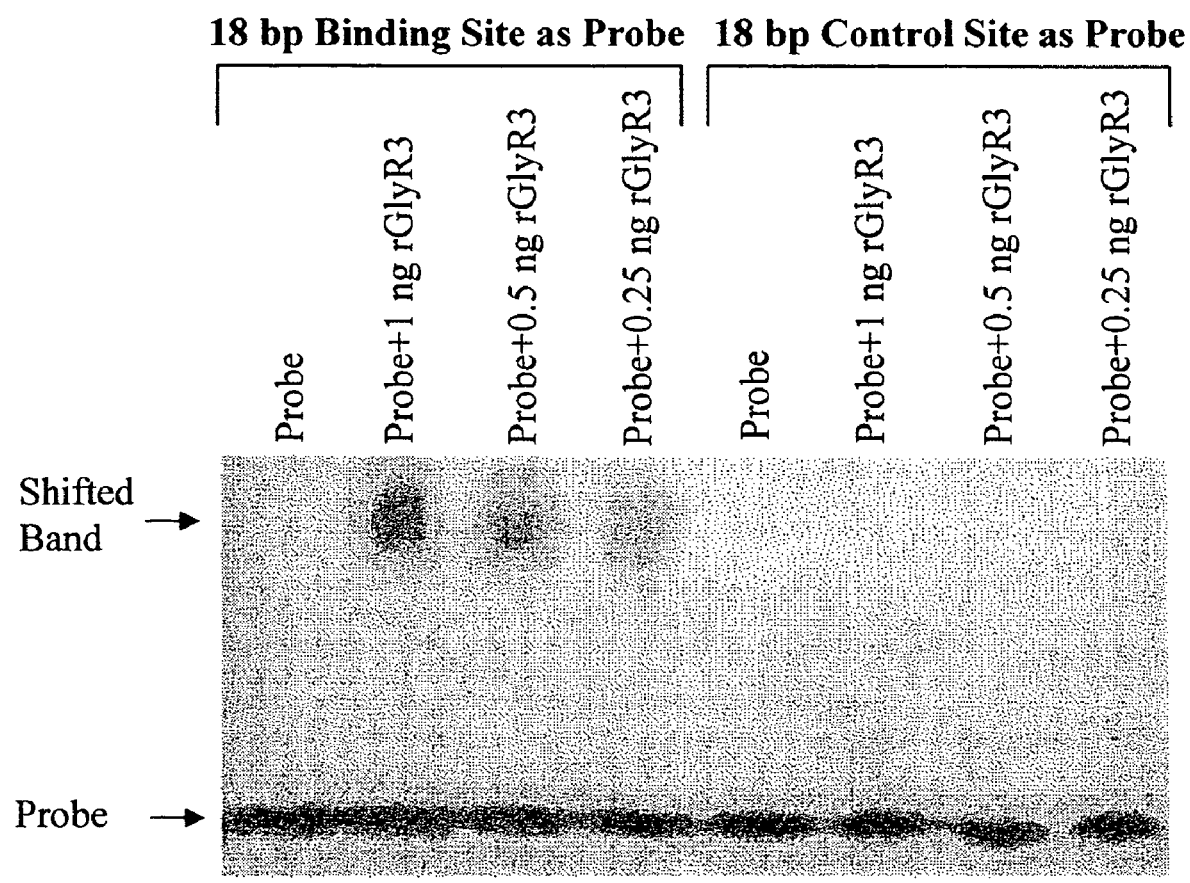
FIG. 13 shows the results of an EMSA experiment showing that rGlyR3 has dose dependent binding to the 18 bp DNA fragment. Also, rGlyR3 shows no binding to a control fragment of 18 bp that is located within the celC promoter.

Binding of rGlyR3 to the celC Promoter Region rGlyR3 was shown to bind to the celC promoter region. The dissociation constant was determined as the concentration of GlyR3 needed to shift 50% of the celC promoter region in the EMSA. The apparent Kd was determined to be $4\times10^{-14}$ M. Results of binding studies are shown in FIGS. 11-13. As FIG. 11 shows, GlyR3 binds specifically to the celC promoter region. The first and second halves of the celC promoter are used as probes, FIG. 11, lanes 1 and 3 (5 ng each). rGlyR3 (0.5 ng) creates a shifted band with both probes, signifying binding to both fragments, as shown in FIG. 11, lanes 2 and 4. A 200 bp fragment of the celS structure gene was used as probe as shown in FIG. 11, lane 5. Because rGlyR3 does not bind to this DNA fragment, no shift is observed in the EMSA in FIG. 11, lane 6.

As shown in FIG. 12, GlyR3 (1 ng) binds to the 200 bp celC promoter region (5 ng)(lane 2). A truncated version of the GlyR3 protein, that does not contain the N-terminal DNA binding domain, fails to bind to the same promoter region, as shown in FIG. 12, lane 3.

As shown in FIG. 13, rGlyR3 demonstrates dose dependent binding to the 18 bp DNA fragment. rGlyR3 shows no binding to a control fragment of 18 bp that is located within the celC promoter. This 18 bp fragment has been identified, as described in Example 13.

Example 13

GlyR3 DNA Binding Sequence Determination by DNase I Footprint

Figure 14:
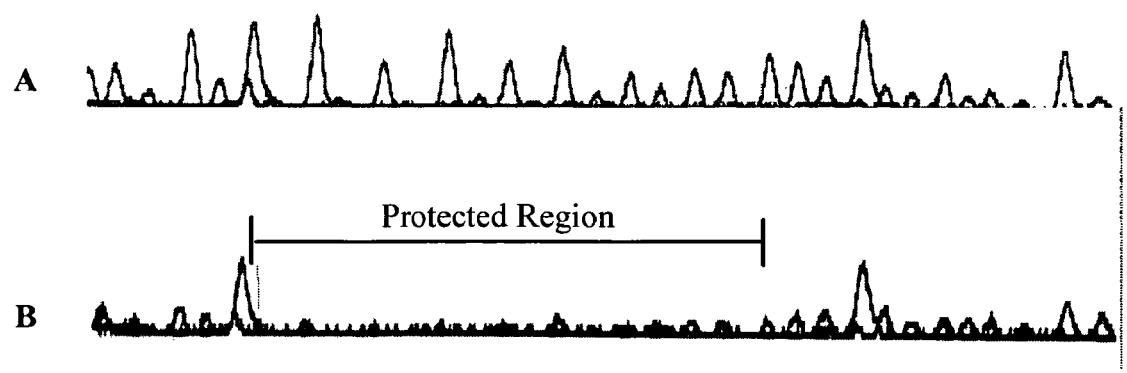
FIG. 14 shows result of DNase I footprint of the first binding site. The 200 bp CelC promoter region was end labeled with fluorescein, the GlyR3 protein bound to the DNA and the binding reaction was subjected to DNase I digestion. A control reaction containing no protein was used to determine where the protein-protected region was located. A, Control peak pattern; B, DNase I subjected peak pattern
Figure 15:
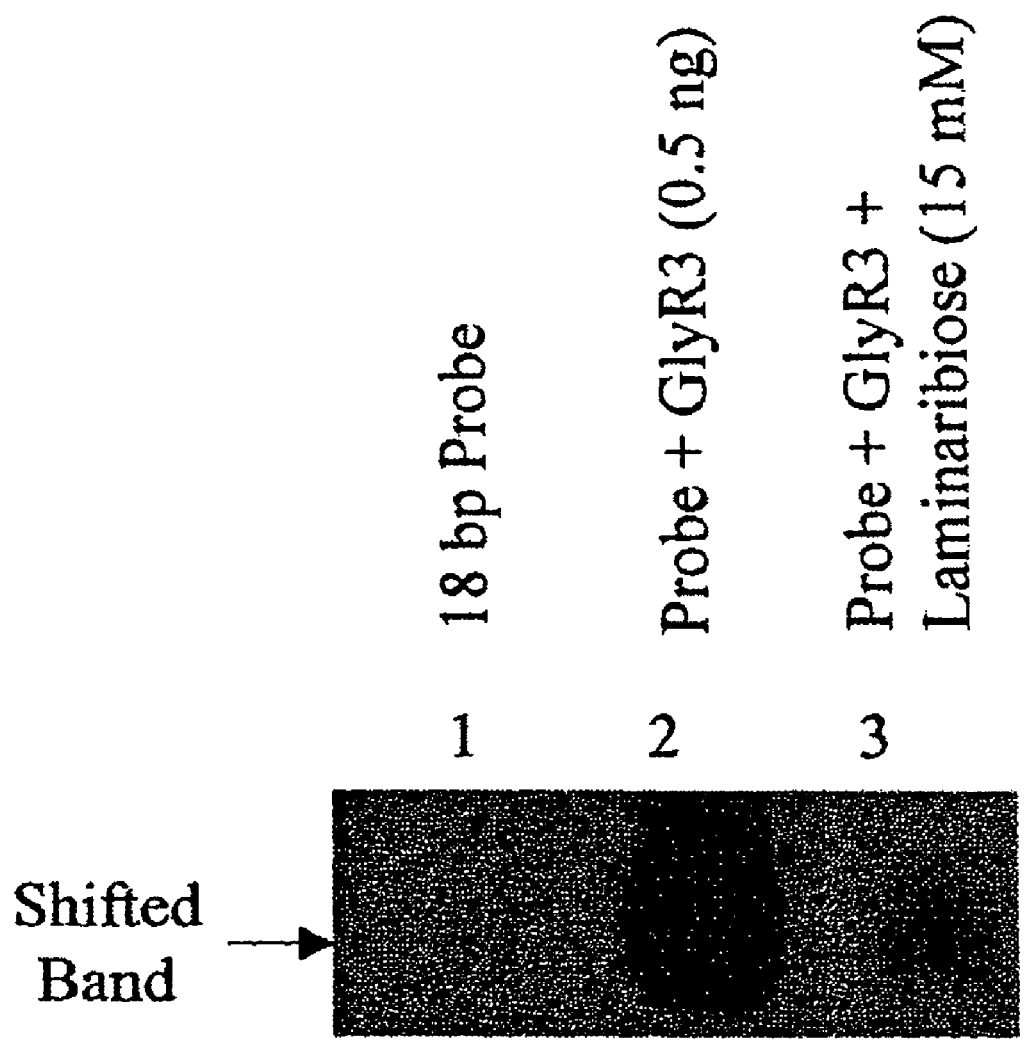
FIG. 15 is result of an EMSA assay indicating that binding of GlyR3 to the 18 bp binding site is inhibited by laminaribiose.

A DNase I footprint assay was used to discern the binding sequence of GlyR3 on the celC promoter region. The celCProm-F primer was end-labeled with fluorescein (Invitrogen, Carlsbad, Calif.) instead of biotin. PCR was used to amplify the 200 bp celC promoter region with celCProm-F-Fluorescein and celCProm-R-unlab. Control and sample mixtures containing 400 ng of the amplified fragment, 1× Lightshift Chemiluminescent EMSA kit binding buffer (Pierce Biotechnology) (10 mM Tris, 50 mM KCl, 1 mM DTT), and 300 ng dI-dC were created. 60 ng of rGlyR3 was added to the sample mixture. DNase I (Invitrogen, Carlsbad, Calif.) (1 U) was added to each mixture. After incubation for 7 minutes at 37° C., 1 mM EDTA was added to each mixture and they were heated to 70° C. for 15 minutes. A Genetic Analyzer 3000 was used to analyze the mixtures at the University of Rochester Functional Genomics Center. Comparing the two results it was possible to see where the rGlyR3 bound to the DNA, protecting it from DNase I digestion, as shown in FIG. 14.

Figure 16:
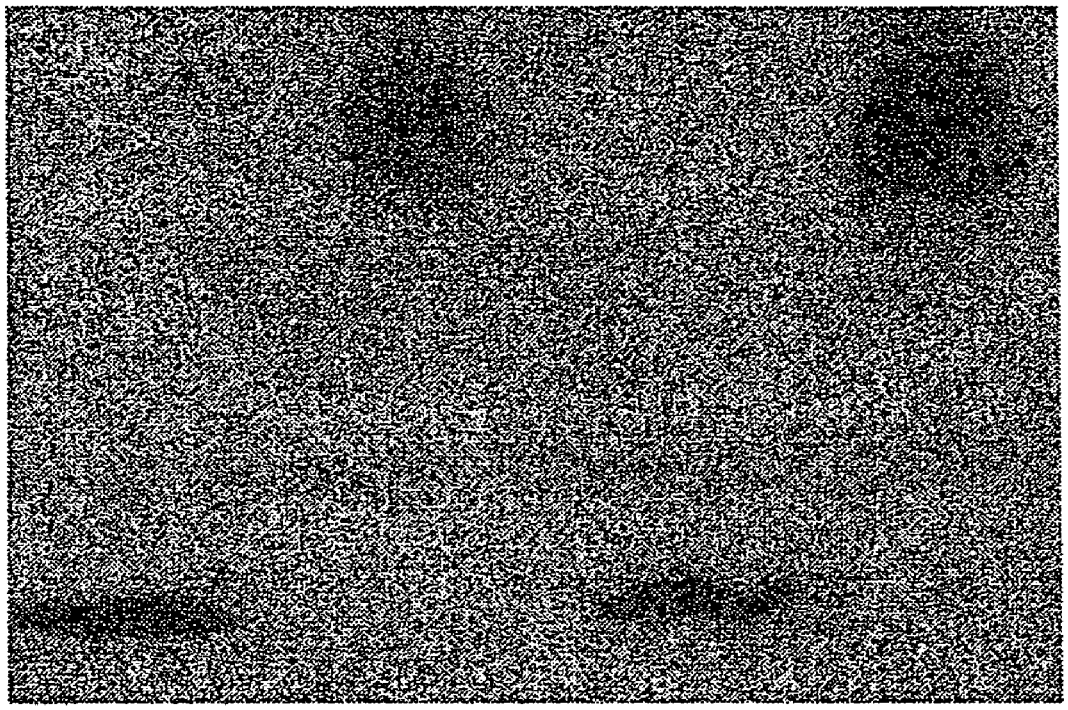
FIG. 16 is a gel showing the results of an EMSA rGlyR3 binding site competition assay. A gel shift competition assay was used to analyze specificity of binding and confirm the DNase I footprint results. All lanes contain biotin labeled 100 bp celC promoter fragment containing the binding site. Lane 1, no protein; Lane 2, 0.5 ng rGlyR3; Lane 3, 0.5 ng rGlyR3 and 100× unlabeled 18 bp binding site; Lane 4, 0.5 ng rGlyR3 and 100 × control fragment (18 bp piece of original 100 bp region, contains no part of putative binding site).

The protected region was shown to be an 18 bp near perfect palindromic sequence located in the nucleic acid molecule having (SEQ ID NO:1), the celC promoter sequence). The 18 bp sequence corresponds to (SEQ ID NO:36): AATGAACGC GCGTACATT. To check the results of the footprint assay an EMSA competition experiment was carried out, as shown in FIG. 16. The competition EMSA showed that 100× of the unlabeled 18 bp binding site was able to compete out the shifted band from a 100 bp piece of the celC promoter region, aa shown in FIG. 16, lane 3. A 100× unlabeled 18 bp piece of the celC promoter that did not contain the binding site was unable to compete out the shifted band, as shown in FIG. 16, lane 4.

Example 14

Laminaribiose Effect on the GlyR3-celC Promoter Binding

Figure 17:
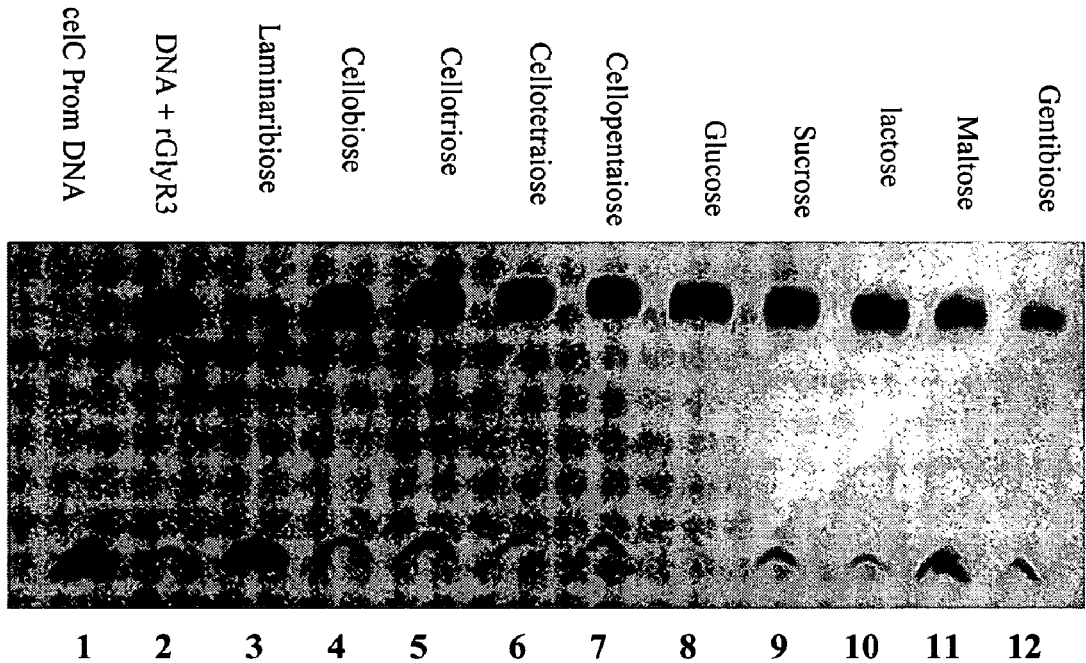
FIG. 17 shows results of an EMSA to assay binding activity of rGlyR3 with celC promoter region when subjected to different sugars. The EMSA analyzing biotin labeled DNA fragments. Lane 1, no protein and 5 ng DNA; Lanes 2-12 contain 5 ng 100 bp celC promoter DNA, 0.5 ng rGlyR3 and 15 mM of their respected sugars.

The binding of the rGlyR3 protein was inhibited by laminaribiose. Several sugars were tested to see if they could inhibit the rGlyR3-celC promoter complex. Cello-bi-tri-tetra and pentose, as well as, glucose, sucrose, lactose, maltose and gentibiose all showed no effect on the binding reaction, as shown in FIG. 17. Only laminaribiose severely reduced the formation of the DNA-protein complex, as shown in FIG. 17, lane 3.

Example 15

GlyR3 Sequence Homology

The draft sequence of *Clostridium thermocellum* was searched for possible transcriptional regulators.

TABLE 1

The binding half site of GlyR3 compared to similar repressor proteins in other organisms. Some exemplary ones are shown below in Table 1.*

| Regulator | Sequence | | Species |
|---|---|---|---|
| GlyR3 | AATGAACGC | (SEQ ID NO:37) | *C. thermocellum* |
| CelR | TGGGAGC | (SEQ ID NO:38) | *T. fusca* |
| LacI | TTGTGAGC | (SEQ ID NO:39) | *E. coli* |
| CcpA | TGTAAGC | (SEQ ID NO:40) | *B. subtillis* |
| GalR | GTGKAANC | (SEQ ID NO:41) | *E. coli* |
| GalS | GTGKAANC | (SEQ ID NO:42) | *E. coli* |

K = G/T
N = Any base
*Spiridonov et al. J. Biol. Chem., 274, 13127, (1999), which is hereby incorporated by reference in its entirety Discussion
Cellulase Synthetase Cellulase synthesis is known to be controlled by transcription regulators. In the fungus *Trichoderma reesei*, a series of activators and repressors have been found to control the levels of cellulase and xylanase. ACEI serves as a repressor (Aro et al., "ACEI of *Trichoderma reesei* is a Repressor of Cellulase and Xylanase Expression," *Appl Environ Microbiol* 69:56-65 (2003)) whereas ACEII (Aro et al., "ACEII, a Novel Transcriptional Activator Involved in Regulation of Cellulase and Xylanase Genes of *Trichoderma reesei*," *Biol Chem* 276: 24309-24314 (2001)) serves as an activator. In addition, CRE1 mediates glucose repression (Aro et al., "ACEI of *Trichoderma reesei* is a Repressor of Cellulase and Xylanase Expression," *Appl Environ Microbiol* 69:56-65 (2003); Aro et al., "ACEII, a Novel Transcriptional Activator Involved in Regulation of Cellulase and Xylanase Genes of *Trichoderma reesei*," *Biol Chem* 276:24309-24314 (2001); Saloheimo et al., "Carbohydrases From *Trichoderma reesei* and other Microorganisms," *Royal Society of Chemistry, Cambridge UK* 267-279). The soil bacteria *Thermobifida fusca* (formerly *Thermomonospora fusca*) has six known cellulase genes, celA-celF. A protein that binds to a 14 bp inverted repeat found in the promoter region of each cellulase gene has been isolated (Spiridonov et al., "Characterization and Cloning of celR, a Transcriptional Regulator of Cellulase Genes from *Thermomonospora fusca*," *Biol Chem* 274:13127-13132 (1999)). This protein, called CelR, serves as a repressor. Binding of CelR to its target DNA sequence is specifically inhibited by low concentrations of cellobiose (0.2-0.5 mM). A mutant of CelR with a slightly modified hinge helix protein structure has confirmed many of these results (14. Spiridonov et al., "A celR Mutation Affecting Transcription of Cellulase Genes in *Thermobifida fusca*," *J Bacteriol* 182:252-255 (2000)). The mutation has been shown to cause weaker DNA binding than the wild type protein. CelR is constitutively expressed with posttranslational modifications affecting its DNA binding activity.

Unlike these microorganisms which produce only free cellulases. *C. thermocellum* produces the cellulosome in addition to free enzymes. A large number of the cellulosome components can be classified into three categories: 1) the scaffolding protein (CipA), 2) the dockerin-containing subunits (such as CelS and many others), and 3) the scaffoldin-anchorage proteins which anchor the cellulosome to the cell surface (such as OlpA, OlpB, and Orf2p). The second category alone comprises more than 60 different genes. The long list of the cellulosomal genes is further complicated by many non-cellulosomal cellulase components produced by this bacterium. The shear number of the genes involved in cellulose degradation suggests that regulation of cellulase biosynthesis in this bacterium is complicated.

Regulation of the cellulosomal cellulase and hemicellulase biosynthesis has been studied in the anaerobe, *C. cellovorans* (Han et al., "Regulation of Expression of Cellulosomal Cellulase and Hemicellulase Genes in *Clostridium Cellulovorans*," *Bacteriol* 185:6067-6075 (2003)). The cellulosomal cellulase and hemicellulase genes are expressed into both monocistronic and polycistronic mRNAs. Transcription starts sites are found 61-233 bp upstream from the first nucleotide of each of the respective translation initiation codons. Some cellulase and hemicellulase genes in this bacterium are coordinately regulated by the carbon source present in the medium (Han et al., "Transcription of *Clostridium Cellulovorans* Cellulosomal Cellulase and Hemicellulase Genes," *Bacteriol* 185:2520-2527 (2003)). Furthermore, a catabolite repression type of mechanism regulates cellulase expression.

In *C. thermocellum*, regulation of CelS, the major component of the cellulosome, has been studied at the protein level using western blot. The results indicate that CelS production is higher on cellulose than cellobiose (Dror et al., "Regulation of the Cellulosomal CelS (cel48A) Gene of *Clostridium thermocellum* is Growth Rate Dependent," *Bacteriol* 185:3042-3048 (2003)). Quantitative RNase protection assay revealed that the level of celS mRNA under carbon or nitrogen limitation in a chemostat is a function of the growth rate, lower rate favoring celS expression. Two major transcriptional start sites are found 145 and 140 bp upstream of the translational start site, respectively. The relative activities of the two promoters remain constant under the expression conditions. Similar experiments have been done with the scaffoldin-related genes of the bacterium (Dror et al., "Regulation of Expression of Scaffoldin-Related Genes in *Clostridium thermocellum*," *Bacteriol* 185:5109-5116 (2003)). The transcription levels of cipA, olpB, and orf2A vary with the growth rate under nitrogen or carbon limitation. On the other hand, expression of sdbA is independent from the growth rate. Two transcription start sites have been found 81 and 50 bp upstream of the CipA translational start site, respectively. Transcription from the first promoter ($\sigma^L$-like) occurs under all growth conditions, whereas expression from the second promoter ($\sigma^A$-like) occurs only under carbon limitation.

So far, no transcription regulators have been reported in *C. thermocellum*. Identifying such regulators will be an important step in understanding the control of cellulase biosynthesis in this bacterium. Toward this end, we have taken a bioinformatic approach to study this undoubtedly complicated regulatory system at the molecular level. It is presumed that, given the complexity of the cellulase system in this bacterium, there are multiple control mechanisms involved. On the other hand, our discovery of three LacI-like proteins, each containing a DNA- and a sugar-binding domains, indicates that negative regulation plays an important role in the control scheme. In particular, glyR3 is located within an operon-like gene cluster, suggesting that coordinate regulation of multiple genes in the form of an operon exists in *C. thermocellum*. Furthermore, the fact that glyR3 is a member of this gene cluster suggests that GlyR3 controls its own expression and that expression of the gene cluster depends on the continuous availability of an inducer. The inducer would upregulate the repressor (GlyR3) which in turn calls for more inducer.

It is of note that the gene cluster comprises both the cellulosomal (ManB and CelT) and non-cellulosomal (CelC and LicA) components of the glycosyl hydrolase system. It is possible that all of these genes are coordinately regulated. If this is the case, the regulation mechanisms in this bacterium, as a general rule, may not discriminate between the cellulosomal and non-cellulosomal enzyme components. Instead, the genes involving in a particular physiological process, regardless of whether the proteins encoded are associated with the cellulosome, may be coordinately regulated. Our discovery that laminaribiose, β-1,3 linked disaccharide, serves as an inducer suggests that these genes are related to the breakdown of polysaccharide(s) containing β-1,3 linkage. On the other hand, the function of the putative transporter, which is the fourth member of the gene cluster, remains to be elucidated.

Negative Regulation

The task of elucidating the mechanisms controlling the biosynthesis of biomass-degrading enzymes in clostridia is obviously complicated by the large number of the genes and proteins involved. In *C. thermocellum*, the long list of the cellulosomal genes is further complicated by many non-cellulosomal enzyme components. -The large number of the genes involved necessitates the use of a genomics approach. By searching the genome, three *C. thermocellum* proteins, GlyR1, GlyR2, and GlyR3 (formerly CelR1, CelR2, and CelR3, respectively) have been identified that are homologous to the *E. coli* Lac. Each of these putative regulatory proteins contains two major domains. A helix-turn-helix DNA-binding domain is N-terminal to a sugar-binding domain. The domain structure of the GlyR proteins is thus similar to the LacI structure and suggests that they belong to the Lac I family of negative regulators. Among them, GlyR3 is encoded by a member of the celC gene cluster mentioned above, including the genes encoding CelC, GlyR3, LicA, a putative membrane protein, ManB, and CelT, respectively. The DNA-binding domain of GlyR3 shows a helix-turn-helix structure very similar to that of LacI. On the other hand, the folding of the sugar-binding domain of GlyR3, as predicted by homology modeling, is substantially different from its equivalent in LacI. The results are consistent with the expectation that GlyR3 is a DNA-binding protein regulated by a sugar other than lactose. Experimental evidence indicates that GlyR3 binds to the celC promoter region and such binding is specifically inhibited by laminaribiose. Thus laminaribiose appears to serve as an inducer of the gene cluster by inactivating binding of GlyR3 to the promoter region. This is the first demonstration, after a long search for transcription regulators of the *C. thermocellum* cellulase system, that the cellulase genes can be regulated by negative control. The demonstration will undoubtedly prompt efforts to find additional transcription factors that regulate cellulase formation in clostridia. Thorough understanding of the cellulase and hemicellulase regulatory mechanisms will be crucial for deregulating their production through rational genetic manipulations.

What is claimed:

1. A nucleic acid construct comprising:

an isolated nucleic acid promoter suitable for directing expression of a protein or polypeptide encoded by a nucleic acid molecule operably associated with the nucleic acid promoter, wherein the nucleic acid promoter has a nucleotide sequence of SEQ ID NO:;

a first nucleic acid molecule, the first nucleic acid molecule encoding the protein or polypeptide;

a first regulatory region;

a second nucleic acid molecule, the second nucleic acid molecule encoding a repressor protein;

a second regulatory region; and a third regulatory region;

wherein the isolated nucleic acid promoter, the first nucleic acid molecule, and the first regulatory region are operably linked together to allow expression of the protein or polypeptide;

wherein the second nucleic acid molecule, the second regulatory region, and the third regulatory region are operably linked together to allow expression of the repressor protein; and wherein the second and third regulatory regions are the same regulatory regions linked to the first nucleic acid molecule.

2. The nucleic acid construct according to claim 1, wherein the first nucleic acid molecule encodes a therapeutic protein or an enzyme.

3. The nucleic acid construct according to claim 2, wherein the first nucleic acid molecule encodes an enzyme capable of degrading a cellulosic substrate or constituting part of a metabolic pathway.

4. The nucleic acid construct according to claim 3, wherein the first nucleic acid molecule encodes an enzyme selected from the group consisting of cellulase, hemicellulase, endoglucanase, exoglucanase, xylanase mannanase, lichenase, chitinase, glycosidases, esterases, lyase, lignase, lignin degrading enzyme, alcohol dehydrogenase, and pyruvate decarboxylase.

5. A nucleic acid construct comprising:
an isolated nucleic acid promoter suitable for directing expression of a protein or polypeptide encoded by a nucleic acid molecule operably associated with the nucleic acid promoter, wherein the nucleic acid promoter has a nucleotide sequence of SEQ ID NO:1;
a first nucleic acid molecule, the first nucleic acid molecule encoding the protein or polypeptide;
a first regulatory region;
a second nucleic acid molecule having a nucleotide sequence of SEQ ID NO: 2, the second nucleic acid molecule encoding a repressor protein;
a second regulatory region; and
a third regulatory region;
wherein the isolated nucleic acid promoter, the first nucleic acid molecule, and the first regulatory region are operably linked together to allow expression of the protein or polypeptide; and
wherein the second nucleic acid molecule, the second regulatory region, and the third regulatory region are operably linked together to allow expression of the repressor protein.

6. An expression vector comprising the nucleic acid construct according to claim 5.

7. A host comprising the expression vector according to claim 6, wherein the host is a bacterial cell, a yeast cell, a fungal cell, an insect cell, a mammalian cell, or a virus.

8. The host according to claim 7, wherein the host is a cellulase, hemicellulase, or ethanol producer.

9. The host according to claim 7, wherein the host is a bacterial cell selected from the group consisting of *Clostridium* spp., *Zymomonas* spp., *E. coli*, or *Thermoanaerobacterium saccharolyticum*.

10. A method of producing ethanol from a biomass, said method comprising:
providing a first host comprising a first nucleic acid construct, the first nucleic acid construct comprising:
an isolated nucleic acid promoter suitable for directing expression of a protein or polypeptide encoded by a nucleic acid molecule operably associated with the nucleic acid promoter, wherein the nucleic acid promoter has a nucleotide sequence of SEQ ID NO:1;
a first nucleic acid molecule, the first nucleic acid molecule encoding a protein or polypeptide; and
a first regulatory region, wherein the nucleic acid promoter, the first nucleic acid molecule, and the first regulatory region are operably linked together to allow expression of the protein or polypeptide;
providing a second host comprising a second nucleic acid construct, the second nucleic acid construct comprising:
a second nucleic acid molecule, the second nucleic acid molecule encoding a repressor protein having an amino acid sequence of SEQ ID NO:3;
a second regulatory region; and
a third regulatory region, wherein the second and third regulatory regions are operably linked to the second nucleic acid molecule to allow expression of the repressor protein; and
contacting a biomass with the first host and the second host under conditions effective to allow production of ethanol from the biomass.

11. The method according to claim 10, wherein the conditions effective to allow production of ethanol from the biomass comprise contacting the first host with an inducing agent, wherein the inducing agent is lichenan, laminarin, laminaribiose, laminaritriose, laminaritetreose, laminaripentaose, an oligosaccharide containing 1,3 linked sugar residues, a polysaccharide containing 1,3 linked sugar residues, or any analog thereof.

12. The method according to claim 10, wherein the first host is a yeast cell, a fungal cell, or a bacterial cell.

13. The method according to claim 12, wherein the first host is a cellulase, hemicellulase, or ethanol producer.

14. The method according to claim 13, wherein the first host is a bacterial cell selected from the group consisting of *Clostridium* spp., *Zymomonas* spp., *E. coli*, or *Thermoanaerobacterium saccharolyticum*.

15. The method according to claim 10, wherein the second host is a yeast cell, a fungal cell, or a bacterial cell.

16. The method according to claim 15, wherein the second host is a cellulase, hemicellulase, or ethanol producer.

17. The method according to claim 10, wherein the second host is a bacterial cell selected from the group consisting of *Clostridium* spp., *Zymomonas* spp., *E. coli*, or *Thermoanaerobacterium saccharolyticum*.

18. The method according to claim 10, wherein the biomass is a cellulosic substrate.

19. A nucleic acid construct comprising:
a nucleic acid promoter, wherein the nucleic acid promoter has a nucleotide sequence of SEQ ID NO:1;
a first nucleic acid molecule, the first nucleic acid molecule encoding a protein or polypeptide;
a first regulatory region;
a second nucleic acid molecule, the second nucleic acid molecule encoding a repressor protein;
a second regulatory region; and
a third regulatory region;
wherein the nucleic acid promoter, the first nucleic acid molecule, and the first regulatory region are operably linked together to allow expression of the protein or polypeptide;
wherein the second nucleic acid molecule, the second regulatory region, and the third regulatory region are operably linked together to allow expression of the repressor protein; and
wherein the second and third regulatory regions are the same regulatory regions linked to the first nucleic acid molecule.

20. The nucleic acid construct according to claim 19, wherein the first nucleic acid molecule encodes a therapeutic protein or an enzyme.

21. The nucleic acid construct according to claim 20, wherein the first nucleic acid molecule encodes an enzyme capable of degrading a cellulosic substrate or constituting part of a metabolic pathway.

22. The nucleic acid construct according to claim 21, wherein the first nucleic acid molecule encodes an enzyme selected from the group consisting of cellulase, hemicellulase, endoglucanase, exoglucanase, xylanase mannanase, lichenase, chitinase, glycosidases, esterases, lyase, lignase, lignin degrading enzyme, alcohol dehydrogenase, and pyruvate decarboxylase.

23. The nucleic acid construct according to claim 19, wherein the second nucleic acid molecule has a nucleotide sequence of SEQ ID NO:2.

24. An expression vector comprising the nucleic acid construct according to claim 19.

25. A host comprising the expression vector according to claim 24, wherein the host is a bacterial cell, a yeast cell, a fungal cell, an insect cell, a mammalian cell, or a virus.

26. The host according to claim 25, wherein the host is a cellulase, hemicellulase, or ethanol producer.

27. The host according to claim 25, wherein the host is a bacterial cell selected from the group consisting of *Clostridium* spp., *Zymomonas* spp., *E. coli*, or *Thermoanaerobacterium saccharolyticum*.

28. A method for directing expression of a protein or polypeptide in a host, said method comprising:
transforming a host with the nucleic acid construct according to claim 19 to produce a transformed host, under conditions effective to allow expression of the protein or polypeptide in the host.

29. The method according to claim 28, wherein the conditions effective to allow expression of the protein or polypeptide in the host comprise contacting the host with an inducing agent.

30. The method according to claim 29, wherein the inducing agent is lichenan, laminarin, laminaribiose, laminaritriose, laminaritetreose, laminaripentaose, a synthetic inducer, an oligosaccharide containing 1,3 linked sugar residues, a polysaccharide containing 1,3 linked sugar residues, or any analog thereof 31. The method according to claim 28, wherein the host is a bacterial cell, a fungal cell, a yeast cell, an insect cell, a mammalian cell, or a virus.

32. The method according to claim 31, wherein the host is a bacterial cell selected from the group consisting of *Clostridium* spp., *Zymomonas* spp., *E. coli*, or *Thermoanaerobacterium saccharolyticum*.

33. A method for directing in vitro expression of a protein or polypeptide, said method comprising:
providing a cell-free transcription-translation system;
providing a nucleic acid template for the cell-free transcription-translation system using the nucleic acid construct according to claim 19; and
combining the nucleic acid template with the cell-free transcription-translation system under conditions effective to allow expression of the protein or polypeptide in vitro.

34. A method for directing inducible in vivo expression of a protein or polypeptide in a host, said method comprising:
transforming a host with the nucleic acid construct according to claim 19 to produce a transformed host, under conditions effective to allow expression of the protein or polypeptide in the host.

35. The method according to claim 34, wherein the conditions effective to allow expression of the protein or polypeptide in the host comprise contacting the host with an inducing agent, wherein the inducing agent is lichenan, laminarin, laminaribiose, laminaritriose, laminaritetreose, laminaripentaose, a synthetic inducer, an oligosaccharide containing 1,3 linked sugar residues, a polysaccharide containing 1,3 linked sugar residues, or any analog thereof.

36. The method according to claim 34, wherein the host is a bacterial cell, a fungal cell, a yeast cell, an insect cell, a mammalian cell, or a virus.

37. The method according to claim 36, wherein the host is a bacterial cell selected from the group consisting of *Clostridium* spp., *Zymomonas* spp., *E. coli*, or *Thermoanaerobacterium saccharolyticum*.

38. A method of producing ethanol from a biomass, said method comprising:
providing a host according to claim 25, and
contacting a biomass with the host under conditions effective to allow the host to convert the biomass to ethanol, thereby producing ethanol from the biomass.

39. The method according to claim 38, wherein the conditions effective to allow the host to convert the biomass to ethanol comprise contacting the host with an inducing agent wherein the inducing agent is lichenan, laminarin, laminaribiose, laminaritriose, laminaritetreose, laminaripentaose, an oligosaccharide containing 1,3 linked sugar residues, a polysaccharide containing 1,3 linked sugar residues, or any analog thereof.

40. The method according to claim 38, wherein the host is a yeast cell, a fungal cell, or a bacterial cell.

41. The method according to claim 40, wherein the host is a cellulase, hemicellulase, or ethanol producer.

42. The method according to claim 38, wherein the host is co-cultured with another organism.

43. The method according to claim 41, wherein the host is a bacterial cell selected from the group consisting of *Clostridium* spp., *Zymomonas* spp., *E. coli*, or *Thermoanaerobacterium saccharolyticum*.

44. The method according to claim 41, wherein the biomass is a cellulosic substrate.

45. An expression vector comprising the nucleic acid construct according to claim 1.

46. A host comprising the expression vector according to claim 45, wherein the host is a bacterial cell, a yeast cell, a fungal cell, an insect cell, a mammalian cell, or a virus.

47. The host according to claim 46, wherein the host is a cellulase, hemicellulase, or ethanol producer.

48. The host according to claim 46, wherein the host is a bacterial cell selected from the group consisting of *Clostridium* spp., *Zymomonas* spp., *E. coli*, or *Thermoanaerobacterium saccharolyticum*.

49. The nucleic acid construct according to claim 5, wherein the first nucleic acid molecule encodes a therapeutic protein or an enzyme.

50. The nucleic acid construct according to claim 49, wherein the first nucleic acid molecule encodes an enzyme capable of degrading a cellulosic substrate or constituting part of a metabolic pathway.

51. The nucleic acid construct according to claim 50, wherein the first nucleic acid molecule encodes an enzyme selected from the group consisting of cellulase, hemicellulase, endoglucanase, exoglucanase, xylanase mannanase, lichenase, chitinase, glycosidases, esterases, lyase, lignase, lignin degrading enzyme, alcohol dehydrogenase, and pyruvate decarboxylase.

* * * * *